United States Patent [19]
Schneider et al.

[11] Patent Number: 5,508,182
[45] Date of Patent: Apr. 16, 1996

[54] ESTERIFICATION OF HYDROPHILIC POLYOLS BY ADSORPTION ONTO A SOLID SUPPORT AND EMPLOYING A SUBSTRATE-IMMISCIBLE SOLVENT

[76] Inventors: Manfred P. Schneider, Triebelsheider Weg 47, D-5600 Wuppertal 1; Kurt E. Laumen, Steinackerweg 10, D-7806 March 2; Matthias Berger, Melchiorstr 24, D-5000 Köln 1, all of Germany

[21] Appl. No.: 193,670

[22] Filed: Feb. 8, 1994

Related U.S. Application Data

[63] Continuation of Ser. No. 834,678, Feb. 12, 1992, abandoned, which is a continuation-in-part of Ser. No. 654,979, Feb. 13, 1991, abandoned.

[51] Int. Cl.$^6$ .................... C12P 7/62; C12P 7/64
[52] U.S. Cl. .................... 435/135; 435/134; 435/174
[58] Field of Search ................ 435/134, 135, 435/174–182

[56] References Cited

U.S. PATENT DOCUMENTS

| | | | |
|---|---|---|---|
| 4,275,011 | 6/1981 | Tanaka et al. | 260/410.7 |
| 4,275,081 | 6/1981 | Coleman | 426/33 |
| 4,614,718 | 8/1984 | Seino et al. | 435/72 |
| 5,079,153 | 1/1992 | Enomoto et al. | 435/126 |
| 5,137,660 | 8/1992 | Mazur et al. | 536/18.2 |

FOREIGN PATENT DOCUMENTS

| | | | |
|---|---|---|---|
| 0035883 | 9/1981 | European Pat. Off. | |
| 3246189 | 5/1983 | Germany | |
| 210263 | 12/1981 | Japan | C12P 7/64 |
| 59-118095 | 7/1984 | Japan | |
| 63-112993 | 5/1988 | Japan | |
| 9001555 | 2/1990 | WIPO | C07K 1/00 |

OTHER PUBLICATIONS

Gardossi L et al, J. Am Chem Soc 113:6328–9 (91).
Nagao A et al., JAOCS 66:710–13 (89).
Hsu S et al, Tetrahedron Lett 31:6403–6 (90).
Ferjancic A, Appl Micro Biol Biotechnol 32:651–7 (1990).
Gatfield, I. L. (1984) Ann. N.Y. Acad. Sci. 434:569–572.
Tsyganov, E. P. et al. (1978) Lab. Delo. 4:221–222.
Wong, C. H., Science 244, 1145–1152 (1989).
Tahoun, M. K. et al., Enzyme Microb. Technol. 8, 429–432 (1986).
Bjorkling, F. et al., J.C.S. Chem. Commun., 934–935 (1989).
Adelhorst, K. et al., Synthesis, 112–115 (1990).
Yamané, T. et al., Ann. N.Y. Acad. Sci. 434, 558–568 (1984).
Hoq, M. M. et al., Agric. Biol. Chem. 49, 335–342 (1985).
Koennecke, A. et al., Montatsh. Chem. 113, 331–337 (1982).
Koennecke, A. et al., Monatsh. Chem. 116, 111–117 (1985).
Holmberg, K. et al., JOACS 65, 1544–1548 (1988).
Zaks, A., JAOCS 66, 484 (1989).
Kuhl, P. et al., Tetrahedron Lett., 31 5213–5216 (1990).
Ferjancic, A. et al., Appl. Microbiol. Biotechnol. 36, 651–657 (1990) (Abstract).
Schuch, R. et al., Appl. Microbiol. Biotechnol. 30, 332–336 (1989).
Eigtved, P. et al., Proc. World Conf. Biotechnol. Fats and Oils, AOCS, 134–137 (1987).
Yamanaka, S. et al., Methods in Enzymol. 136, 405–411 (1987).
Tsyganov, E. P. et al., 1978, "Method for the determination of lipase activity using as the substrate a suspension of triglycerides adsorbed on a solid support." Chemical Abstracts 88:283 (Abstr. No. 185063).
Svensson, I. et al., 1990, "Interestification of phosphatidylcholine with lipases in organic media". Chemical Abstracts 113:630 (Abstr. No. 76595).
The Condensed Chemical Dictionary, Tenth Ed., revised by G. G. Hawley, pp. 557–558.

Primary Examiner—Marian C. Knode
Assistant Examiner—Sandra Saucier
Attorney, Agent, or Firm—Flehr, Hohbach, Test, Albritton & Herbert

[57] ABSTRACT

The invention relates to methods for the production of amphiphilic products such as esters, sugar-esters, peptide-esters, glycolipids, glycoproteins, lipoproteins, peptides, and phosphates of alcohols, sugars, and nucleosides. The methods promote enzymatically catalyzed reactions between hydrophilic substrates such as glycerol, glucose, amino acids, and nucleosides, and second substrates such as free fatty acids, triglycerides, vinylesters, amino acids, and phosphates. The method is also applied to enzymatic reactions with saccharides and polyalcohols. The hydrophilic substrates are adsorbed to finely divided solid supports such as silica gel, diatomaceous earths, or activated charcoals in order to promote the dispersion of the hydrophilic substrates within hydrophobic substrates and solvents. Hydrophobic solvents such as n-hexane and t-butylmethylether may be included in the reaction mixtures.

Reactions are conducted under non-aqueous conditions in order to promote reverse hydrolysis. Methods are provided for the production of isomerically pure 1,3-diglycerides. Further methods are disclosed for the production and specific precipitation of pure 1-monoglycerides through the use of a reactor/separator system. Enzymes used in the methods include lipases from M. mihei and P. fluorescens, glycosidases such as β-galactosidase, proteases such as chymotrypsin, and acid or alkaline phosphatases. Compositions are provided comprising alcohols, carbohydrates, amino acids, or peptides adsorbed onto solid supports such as silica gel.

7 Claims, 7 Drawing Sheets

FIG.—3

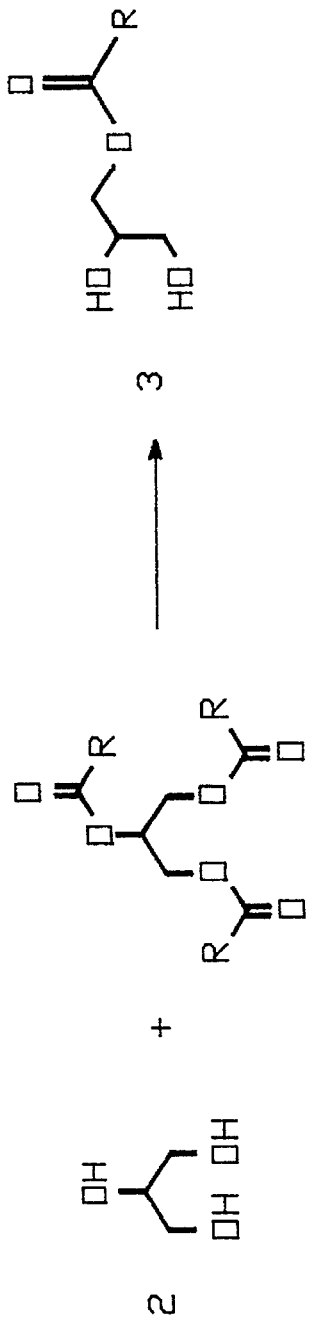
FIG.—5

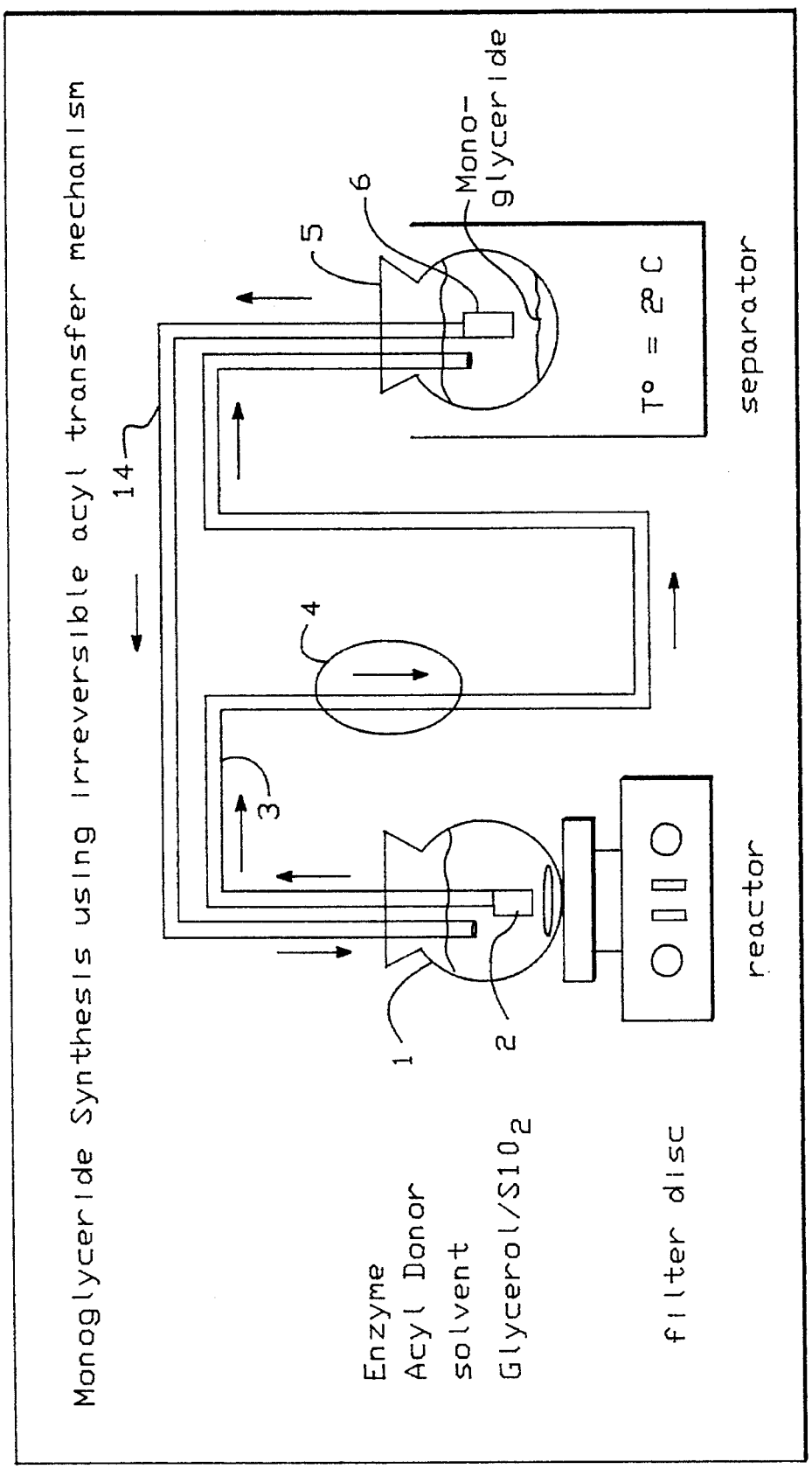
Figure 6 : Acyl donors can be a) Vinyl esters; b) Triglycerides

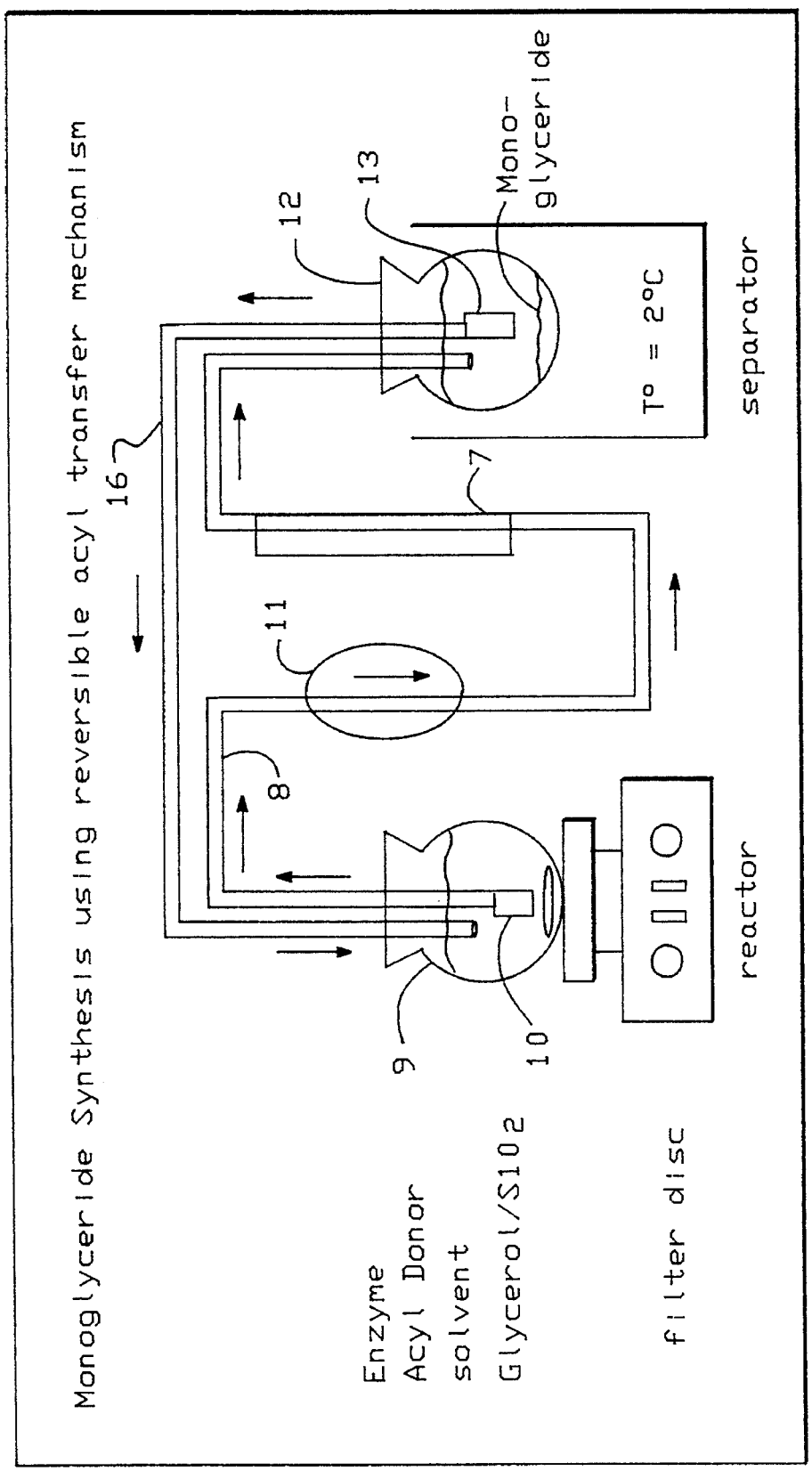
Figure 7 : Acyl donors can be a) Fatty acids; b) FA Alkyl esters

ESTERIFICATION OF HYDROPHILIC POLYOLS BY ADSORPTION ONTO A SOLID SUPPORT AND EMPLOYING A SUBSTRATE-IMMISCIBLE SOLVENT

CROSS-REFERENCE

This is a continuation of application Ser. No. 07/834,678 filed Feb. 12, 1992 now abandoned, which is a CIP of Ser. No. 07/654,979, filed Feb. 13, 1991, now abandoned.

TECHNICAL FIELD OF THE INVENTION

The invention relates to methods for producing amphiphilic compounds through the biocatalyzed reaction of a hydrophilic substrate, adsorbed onto a solid support, with a second substrate, which may be hydrophobic. The invention relates to methods for producing isomerically pure 1,3-diglycerides and 1-monoglycerides, sugar esters, amino acid esters, peptides, and glycolipids, as well as phosphates of alcohols, carbohydrates, and nucleosides. The invention provides compositions of an alcohol or a carbohydrate adsorbed to a solid support and compositions of a carboxyl-protected amino acid or a carboxyl-protected peptide adsorbed to a solid support in combination with an amino-protected amino acid or an amino-protected peptide adsorbed to the same support. The invention also provides methods for the selective precipitation of 1-monoglyceride products.

BACKGROUND OF THE INVENTION

Many chemicals useful in industry are amphiphilic compounds which can be obtained by esterification or reverse hydrolytic reactions between hydrophilic compounds and second compounds, which may be hydrophobic. Illustrations of such reactions follow.

1) Esterification of a polyalcohol:
glycerol+free fatty acid→mono-glyceride+water 2) Esterification of a carbohydrate:
glucose+free fatty acid→sugar-ester+water 3) Esterification of an amino acid:
peptide+free fatty acid→peptide ester+water The amphiphilic products of such reactions are used as surfactants, emulsifiers, food additives, food components, and food substitutes as well as pharmaceuticals. Amino acid and peptide esters possess biological activities similar to those of lipoproteins found in nature, and are potentially useful as pharmaceuticals.

The reactions above are depicted in the direction of reverse hydrolysis, which will dominate only under low water conditions, i.e. in hydrophobic, non-polar solvent. Since the hydrophilic compound is not miscible with non-polar solvent, it is problematic to establish reaction conditions which are favorable to reverse hydrolysis. Moreover, most hydrophilic and hydrophobic compounds are immiscible in one another, and for many compound combinations there is no suitable solvent which would allow the mixing of both substrates. Consequently, esterifications of many hydrophilic compounds, such as glycerol, ethyleneglycol, polyols, and saccharides with long chain fatty acid residues, are difficult or impossible to achieve by traditional means in a batch or column reactor. For instance, the conventional industrial process for the esterification of glycerol with fatty acids is conducted at 200°–250° C. in the presence of an inorganic catalyst, often a toxic metal.

One class of amphiphilic products useful as emulsifiers includes long-chain monoacylglycerols or monoglycerides. Conventionally, they are produced by chemical alcoholysis of the corresponding triglycerides with two equivalents of glycerol (see FIG. 5B). As in industrial esterification, this type of reaction requires high temperatures (210°–240° C.) and the use of transesterification catalysts, usually toxic tin or lead compounds. The reaction product is an equilibrium mixture consisting of monoglyceride, glycerol as well as fatty acids and several contaminating by-products resulting from dehydration processes. In order to yield "pure" monoglycerides, as regioisomers, expensive purification steps are required leading to product yields of only about 40–50% based on the starting glycerides.

Alternatively, chemical multistep processes are reported in the literature based on isopropylidene-glycerol (Bear, E., Fischer, H.O.L., *J. Am. Chem. Soc.* 67, 2031 (1945)) or glycidol (German Patent DE-OS 2,338,462 (1973)).

In these methods, natural starting materials cannot be employed. All the above methods require the synthesis of suitable starting materials and/or protection/deprotection steps. Thus, the above described conventional synthetic methods do not provide convenient means to obtain chemically or isomerically pure monoglycerides.

A potential alternative is offered by biocatalysis utilizing enzymes (for an overview, see Wong, C. H., *Science* 244, 1145–1152 (1989)). In the chemical reactions discussed herein, both of the compounds changed in the reaction are considered substrates for the enzyme (Wong, supra). In order for enzymatic reverse hydrolysis to be made practical for industrial use, the above mentioned problems of substrate/solvent immisibility must be overcome.

Catalysis of esterification reactions by the enzyme lipase has been described. It was reported that, in a reaction between glycerol and free fatty acids, mycelial lipases catalyzed the formation of ester bonds at positions 1 and 3 of glycerol to form mono- and diglycerides (Tahoun, M. K. et al., *Enzyme Microb. Technol.* 8, 429–432 (1986)). Reactions were carried out in aqueous medium, with dispersion promoted by stirring.

Lipases have also been used in the esterification of saccharides with fatty acids (Björkling, F. et al., *J.C.S. Chem. Commun.*, 934–935 (1989); Adelhorst, K. et al., *Synthesis*, 112–115 (1990)). The reactions were conducted without added solvent since the two substrates were somewhat soluble in one another. Water produced in the reactions was removed in vacuo.

For the preparation of monoglycerides, enzymatic multistep processes have been reported based on the starting compounds isopropylideneglycerol (Omar, I. C., Sacki, H., Nishio, N., Nagai, N., *Biotechnol. Lett.* 11, 161 (1989)) or glycidol (Müller, C., Austin, H., Posorske, L., Gruzalez, I., *Novo Industri Publication* A-05991). These enzymatic methods have the same limitations as the chemical multistep processes described above.

In order to increase the rate of reaction and yield, lipase-catalyzed esterification in aqueous medium has been carried out in membrane bioreactors. In the membrane bioreactor system, reverse hydrolysis is promoted through the use of microporous hydrophobic membranes which physically separate the glycerol/water/lipase solution from the fatty acid substrates (Yamane, T. et al., *Ann. N.Y. Acad. Sci.* 434, 558–568 (1984); Hoq, M. M. et al., *Agric. Biol. Chem.* 49, 335–342 (1985)). The fatty acids penetrate the micropores of the hydrophobic membrane sufficiently to participate in the reaction at the interface of the membrane and the aqueous solution; the resulting amphiphilic products remain in the aqueous compartment.

Another approach requires covalent linkage of substrate to a solid support in order to increase the exposure of substrate surface area to reactive groups. Enzymatic peptide synthesis has been promoted in aqueous medium by ester or amide bond linkage of amino acid substrate to activated silicagel (Koennecke, A. et al., *Monatsh. Chem.* 113, 331–337 (1982); Koennecke, A. et al., *Monatsh. Chem.* 111–117 (1985)).

Lipase catalyzed reactions have also been carried out in reverse micellar systems or microemulsions. These systems were designed to promote the exchange of fatty acid side chains on triglycerides. The dispersion of triglycerides in polar solvent was achieved through emulsification with surfactants. When the hydrophilic substrate glycerol was substituted for aqueous buffer in the emulsion system, no ester product was formed. (Holmberg, K. et al., JOACS 65, 1544–1548 (1988); Zaks, A., *JAOCS* 66, 484 (1989)).

Peptide synthesis was reportedly catalyzed by chymotrypsin in an organic solvent, hexane, in which neither the substrates nor the enzyme were soluble (Kuhl, P. et al., *Tetrahedron Lett.*, 31 5213–5216 (1990)). Product yields were inversely proportional to hexane concentration, and fell to zero at moderate concentrations of hexane. Although the authors could offer no conventional explanation for their results, they speculated that the undissolved substrates promoted the reaction through direct particle-particle contact.

Glycoside transfer is another type of reaction which may be enzymatically catalyzed. Products of glycoside transfer include complex oligosaccharides, glycoproteins, and glycolipids. Glycosyltransferases are not yet readily available, but the corresponding hydrolases, i.e. glycosidases (Table 1, category 3.2.1) are commercially available. The glycosidase, β-galactosidase, has been employed to catalyze reactions between saccharides and alcohols. The reported yields were low (25–35%) because the reactions were carried out in an aqueous medium in which the initially formed products were partly decomposed by the hydrolytic action of the enzyme. The reported procedures could not be carried out in non-aqueous medium because of immiscibility of substrates with non-polar solvents.

The problem of enzyme insolubility in organic solvents has been addressed by the adsorption of peptidases and lipases to solid supports such as celite and silicagel (Ferjancic, A. et al., *Appl. Microbiol. Biotechnol.* 36, 651–657 (1990); Schuch, R. et al., *Appl. Microbiol. Biotechnol.* 30, 332–336 (1989); Eigtved, P. et al., *Proc. World Conf. Biotechnol. Fats and Oils*, AOCS, 134–137 (1987); Yamanaka, S. et al., *Methods in Enzymol.* 136, 405–411 (1987)). Amounts of silicagel or celite sufficient to adsorb catalytic amounts of enzyme were either added to the reaction mixture, or, more commonly, were purchased with the enzyme pre-adsorbed onto the support. With stirring, the adsorbed enzyme was dispersed in the hydrophobic solvent. The hydrophilic substrate, however, remained ineffectively dispersed in the solvent which limited the rate of reaction and final product yield.

The hitherto reported phosphorylation of biologically important molecules like glycerol, dihydroxyacetone, enolpyruvate, monosaccharides, and nucleosides was dependent on biological phosphorylating agents, usually adenosine triphosphate (ATP). These reactions reportedly are catalyzed by such enzymes as glycerol kinase and hexokinase, and are carried out in aqueous medium. Such processes are costly because ATP is expensive, is needed in molar amounts, and therefore must be recycled. Recycling of ATP involves a number of additional enzymatic steps and auxiliary reagents.

In addition to limitations in yield and rate of reaction, the published methods leave unsolved the problem of producing isomerically and enantio-merically pure products such as 1-monoglycerides. When glycerides are produced in the above described enzymatic methods, mixtures of monoglycerides with di- and tri-glycerides are obtained. When monoglycerides are isolated from the product mixture, they are always mixtures of regioisomers and stereoisomers. Monoglycerides are classfied according to their absolute configuration as follows.

1-sn-monoglyceride=(S)-1-monoglyceride
3-sn-monoglyceride=(R)-1- monoglyceride
2-sn-monoglyceride=achiral The "sn-" nomenclature is a classification which is exclusively used for glycerides. In the conventional production of monoglycerides as described above, generally mixtures of racemic 1-monoglycerides and achiral 2-glycerides are produced. Such mixtures could be termed as consisting of: (R.S)-1-monoglyceride+2-monoglyceride. Purification steps are required to yield chemically pure monoglycerides as mixtures of regioisomers from which each regioisomer must be separated by tedious chromatographic processes. These processes necessarily operate on a very small scale and are not practical for industrial production.

SUMMARY OF THE INVENTION AND OBJECTS

This invention relates to a method for producing an amphiphilic product through the enzyme catalyzed reaction of a hydrophilic substrate with a second substrate.

According to the present invention, a hydrophilic substrate is dispersed in a second substrate with a selected enzyme so that the reactive groups of both substrates are contacted by the active site of the enzyme and an amphiphilic product is formed. The method comprises combining the hydrophilic substrate with sufficient solid support to substantially adsorb the hydrophilic substrate, and dispersing the adsorbed substrate in the second substrate together with an enzyme which has an affinity towards both substrates and which catalyzes the formation of the product.

If one of the substrates is a liquid, the reaction may proceed without added solvent. If neither substrate is a liquid, it is necessary to include a solvent in the method. It is therefore an object of this invention to provide methods to disperse a hydrophilic substrate in a non-polar or slightly polar solvent which is suitable for use in the processing of food, health care, and cosmetic products.

An object of the invention is to provide methods for the production of pure regioisomers of 1,3-diglycerides.

A further object of the invention is to provide a method for the production of a sugar ester through the enzyme catalyzed reaction of a hydrophilic carbohydrate with a carboxylic acid derivative in a non-polar solvent.

A further object of the invention is to provide methods for the production and specific precipitation of selected 1-monoglycerides in chemically and isomerically pure forms.

A further object of the invention is to provide methods for the production of esters of amino acids.

A further object of the invention is to provide methods for the production of glycosides through the enzymatically catalyzed transfer of glycoside moieties to a polyalcohol.

A further object of the invention is to provide methods for the synthesis of peptides through the enzymatically catalyzed formation of peptide bonds.

A further object of the invention is to provide methods for the enzymatically catalyzed synthesis of phosphates of alcohols, carbohydrates, and nucleosides.

A further object of the invention is to provide compositions comprising alcohols or carbohydrates adsorbed onto a solid support such as silica gel.

A further object of the invention is to provide compositions comprising first and second hydrophilic substrates, both adsorbed to a solid support. In such a composition, the first substrate is a carboxyl-protected amino acid or carboxyl-protected peptide with a free primary amino group, and the second substrate is an amino-protected amino acid or an amino-protected peptide with a carboxylic acid ester.

BRIEF DESCRIPTION OF THE DRAWINGS

FIG. 5 schematically depicts the reactions which yield 1-monoglycerides.

FIG. 6 is a schematic illustration of a reactor/separator system which may be used in the production of a pure 1-monoglyceride from a reaction which does not yield water or alcohol as a by-product and thus goes to completion without removal of products.

FIG. 7 is a schematic illustration of a reactor/separator system which may be used in the production of a pure 1-monoglyceride from a reaction which yields water or alcohol as a by-product. The inclusion of molecular sieves to remove water or alcohol promotes the reaction in the desired direction of esterification.

DETAILED DESCRIPTION OF THE PREFERRED EMBODIMENTS

Figure 1:
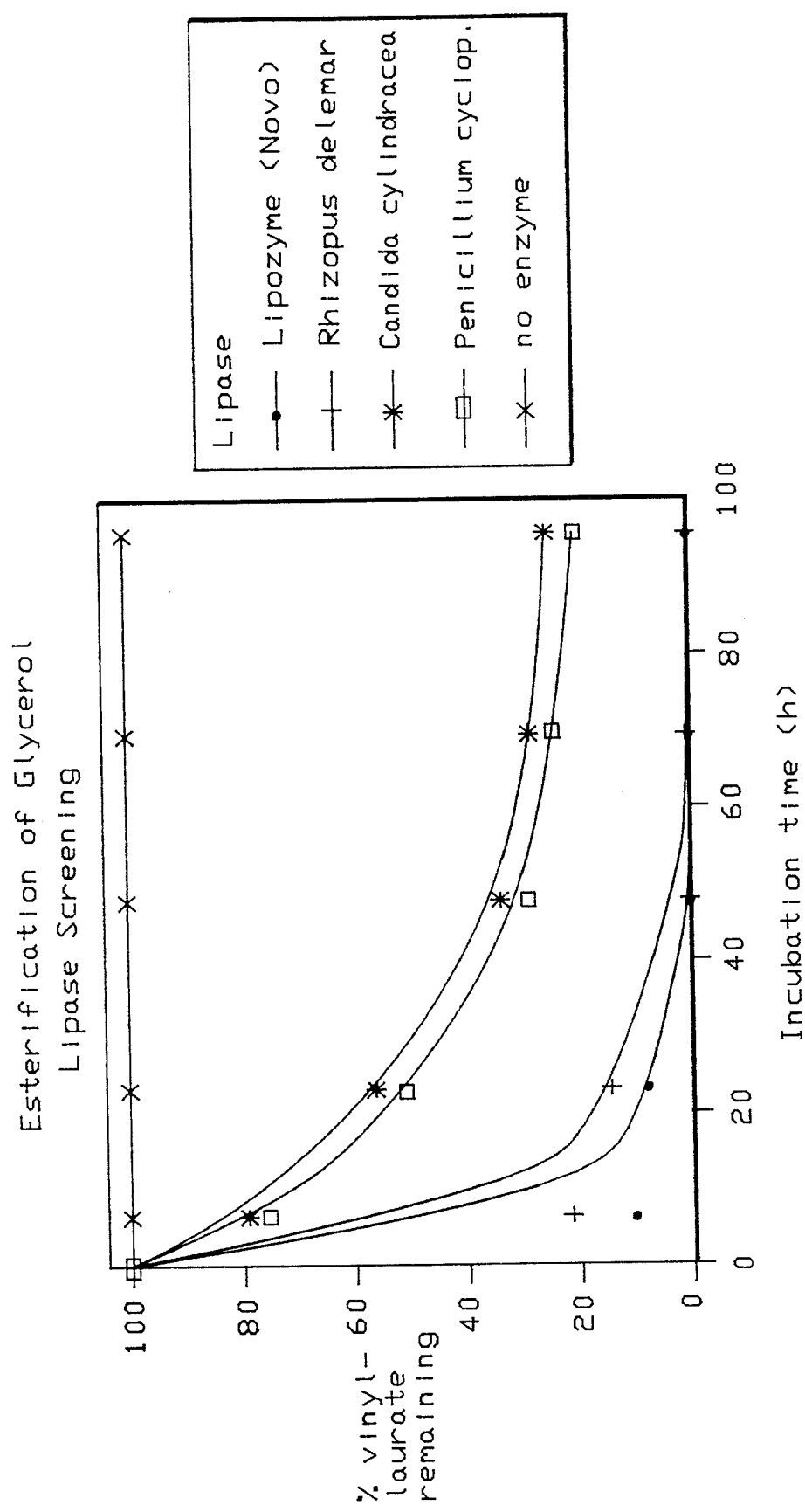
FIG. 1 depicts the effects of different enzyme preparations on the rate of the esterification of glycerol with vinyllaurate.

In the method of the invention, an enzymatically catalyzed reverse hydrolysis reaction is promoted between two substrates by adsorbing the hydrophilic substrate to a solid support and dispersing the adsorbed hydrophilic substrate in the second substrate with a selected enzyme. The hydrophilic substrate adheres to the solid support through a non-covalent interaction, possibly an electrostatic attraction, between the polarized hydroxyl group or amino group of the hydrophilic substrate and the polarized regions of the solid support. The second substrate contains a donatable leaving group (e.g. an acyl group) which probably combines transiently with the enzyme to form an acyl/enzyme intermediate (Wong, supra). It is postulated that, through mixing of the acyl/enzyme intermediate with the adsorbed hydrophilic substrate, the hydroxyl group or amino group of the hydrophilic substrate is brought in contact with the active site of the enzyme and with the donatable leaving group from the second substrate to form an amphiphilic compound. In an alternative embodiment related to peptide synthesis, both substrates contain a hydrophilic region, and both substrates are mixed together prior to adsorbtion onto the solid support.

Definitions

The term "hydrophilic substrate" refers to a water soluble compound containing a hydroxyl group or a primary amino group having the general structure:

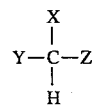

Z can equal OH or $NH_2$. X and Y can equal H, methyl, acyl, allyl, alkyl, aryl, or amino groups. X and Y can also equal methyl, acyl, allyl, alkyl, and aryl groups which have an H substituted by a halogen or by sulphate, phosphate, nitro-, or cyano- groups. Examples of hydrophilic compounds are alkanols, cycloalkanols, benzyl alcohols, allylic alcohols, diols, triols, polyols, sugar alcohols, inositols, halogen substituted alcohols, hydroxycarboxylic acids, amino acids, peptides, saccharides, synthetic and natural polymers with hydroxyl groups.

The term "second substrate having a donatable leaving group" refers to compounds such as carboxylic acids, esters, anhydrides, amino acids with protected or unprotected side chains, peptides, proteins, phosphate esters, glycosides, and substantially hydrophobic alcohols. The donatable leaving group is a chemical moiety for which the enzyme to be employed has an affinity at the enzyme's active site, which can be detached from the second substrate, and which can be covalently linked to a hydroxyl or amino site on the first substrate. The donatable leaving group may be a chemical moiety such as an acyl group, an amino acid residue, a peptidyl group, a protein residue, a phosphoryl group, a glycosidyl residue, or an alkoxide group.

The term "amphiphilic product" refers to a compound which has both hydrophilic and hydrophobic groups. Examples of amphiphilic products include esters, sugar esters, peptides, peptide esters, glycosides, nucleosides, glycolipids, glycoproteins, lipoproteins, phosphates, and sulphates.

The term "ester" refers to the product of the reaction between a polyol, a carbohydrate, an amino acid, or a peptide and the donor of an acyl group such as a long chain fatty acid. The hydrophilic moieties in the ester are polarized groups such as unreacted hydroxyl groups and the hydrophobic moieties are, for instance, long carbon chains which have replaced a hydroxyl group on the starting substrate polyalcohol or carbohydrate. Examples of esters are mono-, di-, and triglycerides, which are the products of reactions between glycerol and donors of carbon chains such as free carboxylic acids, carboxylic esters and carboxylic vinylesters.

The term "glycoside" refers to a compound which contains at least one sugar residue. Examples of glycosides are oligosaccharides, glycoproteins, nucleosides, and glycolipids.

The term "enzyme" refers to a proteinaceous catalyst capable of accelerating reverse hydrolysis reactions selected from the list in Table 1. Additional examples for enzymes useful in practicing this invention are found in the following references: Barman, T. E., *Enzyme Handbook*, Springer-Verlag, N.Y. Vol II, pp. 602–649, 1985; Sigma Chemical Company Catalog, St. Louis, Mo., pp. 863–869, 1991. The appropriate enzyme for a desired reaction product is chosen for its affinity and specific activity towards both the hydrophilic substrate and the second substrate. The appropriate enzyme recognizes one or more of the donatable leaving groups of the second substrate according to the regiospecific position and inherent characteristics of the leaving group, e.g. position 1, 2, or 3 of a triglyceride, chain length, degree of saturation. The appropriate enzyme also has an affinity for and reactivity towards the hydroxyl or amino group of the hydrophilic first substrate based on the size and local electrical charge of chemical moieties surrounding the group. The enzyme may be obtained from a microbial source, or from plant or animal cells or tissues. The enzyme may be purified or included in a crude, relatively impure mixture of several different types of enzymes. The enzyme preparation may be in any form such as a lyophilized powder, or covalently linked or adsorbed onto a solid support.

TABLE 1

Enzymes which catalyze reverse hydrolytic reactions. Numbering and classification according to the convention of the International union of Biochemistry (IUB) (Enzyme Nomenclature 1978, Academic Press, New York 1979).

2. Transferases
  2.3  Acyltransferases
      2.3.1  Acyltransferases
      2.3.2  Aminoacyltransferases
  2.4  Glycosyltransferases
      2.4.1  Hexosyltransferases
      2.4.2  Pentosyltransferases
  2.7  Transferring phosphorus-containing groups
      2.7.1  Phosphotransferases with an alcohol group as acceptor
      2.7.2  Phosphotransferases with a carboxyl group as acceptor
      2.7.3  Phosphotransferases with a nitrogeneous group as acceptor
      2.7.4  Phosphotransferases with a phospho-group as acceptor
      2.7.5  Phosphotransferases, apparently intramolecular
      2.7.6  Pyrophosphotransferases
3. Hydrolases
  3.1  Acting on ester bonds
      3.1.1  Carboxylic ester hydrolases
      3.1.2  Thiolester hydrolases
      3.1.3  Phosphoric monoester hydrolases
      3.1.4  Phosphoric diester hydrolases
      3.1.5  Triphosphoric monoester hydrolases
      3.1.6  Sulphuric ester hydrolases
  3.2  Acting on glycosyl compounds
      3.2.1  Glycoside hydrolases
      3.2.2  Hydrolysing N-glycosyl compounds
      3.2.3  Hydrolysing S-glycosyl compounds
  3.3  Acting on ether bonds
      3.3.1  Thioether hydrolases
  3.4  Acting on peptide bonds (peptide hydrolases)
      3.4.1  α-Amino-acyl-peptide hydrolases
      3.4.2  Peptidyl-amino-acid hydrolases
      3.4.3  Dipeptide hydrolases
      3.4.4  Peptidyl-peptide hydrolases
  3.5  Acting on C—N bonds other than peptide bonds
      3.5.1  In linear amides
      3.5.2  In cyclic amides
      3.5.3  In linear amidines
      3.5.4  In cyclic amidines
      3.5.5  In cyanides
      3.5.99  In other compounds
  3.6  Acting on acid-anhydride bonds
      3.6.1  In phosphoryl-containing anhydrides
  4.1  Carbon-carbon lyases TABLE 1-continued Enzymes which catalyze reverse hydrolytic reactions. Numbering and classification according to the convention of the International union of Biochemistry (IUB) (Enzyme Nomenclature 1978, Academic Press, New York 1979).

4.1.1  Carboxy-lyases
      4.1.2  Aldehyde-lyases
      4.1.3  Ketoacid-lyases
  4.2  Carbon-oxygen lyases
      4.2.1  Hydro-lyases
      4.2.99  other carbon-oxygen lyases
  4.3  Carbon-nitrogen lyases
      4.3.1  Ammonia-lyases
      4.3.2  Amidine-lyases
  4.4  Carbon-sulphur lyases
  4.5  Carbon-halide lyases
  4.99  Other lyases The term "solid support" refers to a finely divided material having a large surface area compared to its volume, which is capable of adsorbing hydrophilic compounds. The support material is non-reactive with the substrate chemicals employed and is insoluble in the solvent, when a solvent is used. Examples of solid supports capable of adsorbing hydrophilic materials are silica gels, diatomaceous earths, clays, zeolites, activated charcoals, carboxymethyl cellulose and other substituted celluloses such as cellulose esters, neutral or basic ion exchange resins, porous glass beads, and neutral or basic aluminumoxide. Adsorption onto solid supports makes the hydrophilic substrates dispersable through mixing in hydrophobic substrates. Alternatively, the solid support may be compressed into a stationary column onto which the hydrophilic substrate is adsorbed and through which the hydrophobic substrate is circulated. The solid support provides the basis for the prinicple of improving contact of the hydrophilic substrate with reactive groups within the microenvironment of the enzyme/substrate interphase.

The term "polar solvent" refers to a liquid compound in which one region of the molecule has higher electronegativity than a different region of the same molecule. Generally, hydrophilic compounds are soluble in polar solvents. Very polar solvents such as dimethylformamide, dimethylsulfoxide, dimethylacetamide, or pyridine are frequently unsuitable for use in esterification because they are toxic, difficult to remove and/or recycle. Residual concentrations would render the synthesized product unsuitable for food, cosmetic, and health care applications. Also, many enzymes are inactivated by polar solvents.

The term "non-polar solvent" refers to a liquid compound in which the centers of positive and negative charge essentially coincide or cancel each other so that no dipole moment is produced. In this application, the term "non-polar solvent" also includes those liquid compounds in which the centers of positive and negative charge substantially coincide so that only a small dipole moment is produced, i.e. slightly polar solvents. As a general rule, hydrophobic compounds are soluble in non-polar solvents, while hydrophilic compounds are not soluble in them. Examples of non-polar organic solvents are simple aliphatic hydrocarbons (n-hexane), and aromatic hydrocarbons (toluene). Examples of slightly polar organic solvents are ethers, ketones, and esters. Other examples of slightly polar solvents are chlorinated hydrocarbons (methylenechloride), cyclic ethers (tetrahydrofuran), sterically hindered alcohols (t-butylmethylether), and acetonitrile. Non-polar solvents offer advantages over very polar solvents in that the non-polar or slightly polar solvents can be removed completely by conventional means; thus they are suitable for use in food, pharmaceutical, and cosmetic preparations. The above listed non-polar and slightly polar solvents do not inactivate lipases, as do some highly polar solvents.

According to the method of the present invention, an ester can be prepared rapidly and conveniently by mixing the following:

- a hydrophilic substrate
- a solid support in an amount sufficient to adsorb the hydrophilic substrate
- a second substrate having a donatable leaving group
- an enzyme catalyst
- a non-polar or slightly polar solvent, if necessary or desirable for the specific reaction.

Suitably, the first substrate is glycerol and the second substrate is a free carboxylic acid (fatty acid) which, upon reverse hydrolysis, will yield an amphiphilic ester product plus water. The second substrate may also be a methyl- or alkyl-ester which, upon reverse hydrolysis, will yield an amphiphilic ester product plus an alcohol. These types of reactions are termed "reversible" since the products could participate in the reverse reaction (hydrolysis of the desired ester product) if water or alcohol were allowed to accumulate. The invention may be utilized either with or without the removal of by-products. If water or alcohol is not removed from the product mixture, the reaction will go to equilibrium, which, through reverse hydrolysis or alcoholysis, will yield a certain amount of desired ester product. Preferably, however, water or alcohol is removed from the reaction mixture by the inclusion of a drying agent such as molecular sieves or anhydrous sodium sulphate, in order to allow the continuation of reverse hydrolysis. Alternatively, water or alcohol may be removed by azeotropic distillation in which the solvent mixture is empirically determined to yield selective distillation of water or alcohol.

The method of the invention is also utilized in "irreversible" reactions in which no water or alcohol is produced. Suitably, a second substrate such as a vinyl-carboxylic ester or an isopropenyl-ester is reacted with a first substrate such as glycerol to form the desired ester product plus acetaldehyde or acetone. This type of reaction is termed "irreversible" because the acetaldehyde or acetone products cannot participate in a hydrolytic reaction. Thus the reaction proceeds in the desired direction of reverse hydrolysis without removal of the by-product.

In both the above examples, the "donatable leaving group" on the second substrate is a chain of carbon atoms. According to the present invention, the second substrate having donatable leaving groups is mixed with the hydrophilic substrate adsorbed to solid support, in a low water medium, with the appropriate enzyme. The mixture is agitated at a temperature and for a time sufficient to produce a high yield of amphiphilic product.

The amount of solid support used is proportional to the amount of hydrophilic substrate. When the hydrophilic substrate is an alcohol or a carbohydrate, the ratio of solid support to substrate is preferably in the range of about 0.3:1.0 to about 10.01:1.0, more preferably 5.0:1.0, most preferably 1.0:1.0 (g:g). In the method related to peptide synthesis, both the first and second substrates are hydrophilic, and both substrates are adsorbed to the solid support. In this case, the ratio of solid support to the combined substrates is preferably in the range of about 0.6:1.0 to about 10.0:1:0, more preferably 5.0:1.0, most preferably 1.0:1.0 (g:g).

The ratio of solid support to hydrophilic substrate is selected to assure that at least about 10%, more preferably about 50%, most preferably about 100% of the hydrophilic substrate is adsorbed to solid support. The method of the invention is thus distinguished from previously published methods in which the amount of solid support used was only sufficient to adsorb the catalytic amount of enzyme used. For instance, Schuch et al (supra) reported adding only 5% (w/w) of immobilized enzyme preparation. Thus, even if it is assumed that the entire amount of the support upon which the enzyme was immobilized was available for adsorption of the hydrophilic compound, the proportion of support to hydrophilic compound was no more than 1:20 in the method of Schuch.

In one embodiment of the invention, the hydrophilic substrate may be mechanically mixed with the solid support prior to mixing with the second substrate and the biocatalyst. In a second alternative, the hydrophilic substrate may be disolved in a minimum amount of a polar solvent such as methanol and mixed with the solid support. The hydrophilic substrate adsorbed to solid support is then isolated from the polar solvent by filtration or by evaporation, then mixed with the second substrate and the biocatalyst. In a third alternative, the hydrophilic substrate is mechanically mixed with the solid support and the enzyme to form a slurry, which is then packed into a column through which the second substrate is circulated.

The method of the invention may be practiced with any order of mixing. Thus, the hydrophilic substrate may be pre-adsorbed to solid support as described above. Alternatively, the hydrophilic substrate, the second substrate, and the non-polar solvent, if necessary, may be pre-mixed to form an emulsion prior to addition of solid support and enzyme.

The appropriate enzyme is chosen, according to the desired reaction, from the group listed in Table 1. The enzyme preparation may be free in the form of lyophilized powder, or may be preadsorbed onto a different or the same type of support as the hydrophilic substrate, or may be covalently attached to support.

Suitably, the enzyme is selected from among a family of lipases synthesized by microorganims such as *Mucor mihei, Pseudomonas fluorescens, Rhizopus delemar,* and *Penicillium cyclopium.* A lipase is an enzyme which, in the presence of water, catalyzes the hydrolytic breakdown of fats. In a low water environment, certain lipases catalyze the reverse reaction, reverse hydrolysis, to yield ester products. Individual lipases have selective activity for regioisomeric and enantiomeric forms of the hydrophilic and the hydrophobic substrate. For instance, a 1,3-specific lipase from *Mucor mihei* can promote the production of esters formed exclusively at the 1 and 3 positions of glycerol. Alternatively, a less specific lipase, or a mixture of lipases, may be used in order to obtain triglycerides. Any lipase may be used provided the enzyme exhibits the required substrate specificity or tolerance towards the position, the chain length, and the degree of saturation of the donatable acyl group. The selectivity of the enzyme varies from type to type and determines which types of products are formed. Certain lipases are capable of catalyzing the esterification of amino acids or peptides. The activities of specific lipases may be predicted from descriptions in the volume *Lipases,* ed. Borgstrom, B. and Brockman, H. L., Elsevier, Amsterdam (1984). The enzymes known as glycosidases, e.g.

β-galactosidase, are capable of catalyzing the transfer of glycosyl groups from glycosylated compounds to polyalcohols.

The physical conditions for the reaction, such as temperature, stirring, and pressure, may be tailored according to desired rates and energy input. The temperature used is suitably between about −48° C. and about 100° C., and the reaction typically is run for between about 3 hours and about 3 days. The lower temperature limits are determined by the freezing point of the solvent or of the mixture. For instance, since the freezing point of hexane is about −50° C., the invention method using hexane would necessarily be conducted above −50° C. The optimum temperature and time depend on the specific reaction and the enzyme selected, as illustrated by examples hereinafter. For industrial production, it may be desirable to run the reaction under less than optimal conditions because of savings in energy, or because it may be desirable to leave the reaction vessel unattended for a longer period of time. Thus, the method of the invention promotes convenient and rapid enzymatic reverse hydrolysis, producing high yields of commercially useful amphiphilic products.

The progress of the reactions are measured by conventional means such as chromatography (thin layer, gas, high performance liquid, and the like).

After complete or desired conversions of substrates to products have been achieved, the solid support and the enzyme are removed by conventional means such as simple filtration or centrifugation. Reaction products are isolated with high chemical purities by removal of the organic solvent through conventional means such as evaporation.

In another embodiment of the invention a 1-monoglyceride is selectively produced and precipitated. Suitably, a 1-monoglyceride is produced by the direct esterification of glycerol with a free carboxylic acid or with an alkyl or vinyl ester (FIG. 5A). Alternatively, a 1-monoglyceride may be produced by the esterification of glycerol with carboxylic acid residues from the alcoholysis of a triglyceride; the alcoholysis is catalyzed by the selected enzyme and occurs concomitantly with the esterification reaction (FIG. 5B).

A suitable apparatus for performing this embodiment of the invention is illustrated is FIG. 6. Central to this embodiment is the selection of a solvent or solvent mixture which, when cooled, promotes the selective precipitation of the desired 1-monoglyceride product. In this embodiment, the hydrophilic first substrate is glycerol, which may be adsorbed onto solid support. The glycerol is mixed in a reactor vessel 1 with a selected enzyme, the acyl donor, and the selected solvent. The mixture is stirred in the reactor 1 at a temperature between about −48° C. and about 100° C. The temperature for the reactor is selected, according to the enzyme employed, to allow the enzymatic esterification activity to produce the desired 1-monoglyceride and by-products. The mixture is drawn through a filter disc 2 and transferred through a connector 3 by means of a pump 4 to a separator 5 which is cooled to a temperature which promotes the selective precipitation of the 1-monoglyceride. Under the employed conditions, all other products and unreacted substrates, including 2-mono-, di- and triglycerides, are soluble and remain in the circulating solution. They are drawn through another filter disc 6 and transferred throught a return connector 14 to the reactor 1 where they may again serve as acyldonors for the esterification of glycerol. By selecting the optimum solvent mixture and the optimum temperature for selective precipitation, 1-monoglycerides which are chemically and isomerically pure can be obtained in very high yield without any further purification step.

When the acyl donor is a vinyl or isopropenyl ester or a triglyceride, water or alcohol is not a product of the reaction and the reaction is irreversible. In this case, the reaction will proceed to completion in the desired direction of 1-monoglyceride synthesis without removal of products.

When the acyl donor is a free carboxylic acid or a methyl-or alkyl-ester (FIG. 5A; R'=H, methyl, alkyl), water or an alcohol is a by-product of the reaction; the reaction is reversible and will go only to equilibrium if products are not removed. FIG. 7 illustrates an apparatus in which water or alcohol by-products are removed in the practice of the invention. Molecular sieves 7 of the appropriate pore size are included in the connector 8 to remove water or alcohol and thus promote the reaction in the desired direction of esterification (reverse hydrolysis). Suitably, water is removed by molecular sieves of a pore size of 3 Å, methanol by a pore size of 4 Å. All other components in FIG. 7 are equivalent to those in FIG. 6, i.e. reactor 9, filter disc 10, pump 11, separator 12, filter disc 13, return connector 16.

The molar ratios of glycerol and the corresponding acyldonor may be varied to produce variable mixtures of mono- and diglycerides in the reaction mixture. In order to maximize the yields of the desired monoglycerides, the stoichiometrically appropriate molar ratios of glycerol to acyldonors are employed (e.g. 1 mole glycerol:1 mole donatable acyl group). Where economically desirable, a molar excess of one substrate may be used.

Any lipase may be used that is stable in the selected solvent and that is active towards the acyldonor employed.

If a free fatty acid or its ester is the acyldonor, a lipase is selected that has specificity for the carbon chain characteristics of the acyl group, i.e. chain length, degree of saturation. For instance, lipases from *A. niger* and *G. candidum* are essentially inactive towards lauric acid or laurate esters (see Example 3). If laurate is the acyl donor of choice, the lipase is suitably chosen from *M. mihei, R. delemar*, or *P. fluorescens*, all of which are active towards laurate.

If di- and triglycerides are to be employed as acyldonors, the regiospecificities of the lipases are considered. For instance, the lipase from *M. mihei* has specific activity for the acyl groups at the 1 and 3 positions of di- or triglycerides and leaves the acyl group at the 2 position unreacted. For efficient and quantitative consumption of the acyl donor, preferably lipases with activity also on the 2-position of glycerides are employed. Examples include lipases derived from Pseudomonas species or from *Penicillium cyclopium*.

The optimum solvent mixture and optimum temperatures for reaction and precipitation are empirically determined for each desired mono-glyceride product. Suitably, when the desired product is a 1-monoglyceride, the solvent is a mixture of t-BuOMe:n-hexane in the proportion of about 1:100 to about 1:10, prefereably 1:1 (vol:vol:). Alternatively, when a suitable acyldonor is employed, the solvent may be 100% n-hexane. The solvent composition is entirely dependent on the product desired. For production of 1-monoglyceride, the temperature in the reaction vessel is between about −48° C. to 100° C., more preferable 20° C. to 60° C., most preferably 25° C. to 35° C. For specific precipitation of 1-monoglyceride, the temperature in the separator is between about −49° C. to 15° C., more preferably between about −10° C. to 10° C., most preferably 2° C.

A further embodiment of the invention provides a method for the production of a peptide-ester through the lipase catalyzed reaction of a peptide or an amino acid with a vinyl-ester. Suitably, the alpha-amino groups of the amino acids are protected by the covalently bonded Z-group (Z=carbobenzyloxy). The amino acid or peptide is adsorbed to solid support and reacted with a donatable source of acyl group such as a vinyl-carboxylic acid. Through the catalytic action of the lipase, the carboxylic acid residue is covalently bound to the hydroxyl residue of the amino acid or peptide to form an amino-acid-ester or peptide ester.

A further embodiment of the invention provides methods for the enzymatic production of glycosides such as oligosaccharides, glycoproteins, and glycolipids. Suitably, a hydrophilic first substrate containing a glycosyl moiety is adsorbed to solid support and mixed with a second substrate such as a polyalcohol, and a glycosidase, such as β-galactosidase. The enzyme catalyzes the transfer of glycosyl moities from the first substrate to the hydroxyl groups of the second substrate to form the desired glycoside product.

A further embodiment of the invention provides methods for the enzymatic synthesis of peptides. The hydrophilic first substrate in these reactions is a carboxyl-protected amino acid or peptide with a free primary amino group. The term "carboxyl-protected" refers to an amino acid or peptide in which each carboxyl-group is covalently linked to a group such as a tert-amyl ester, a benzyl ester, or an alkyl ester, which prevents the carboxyl group from participating in the reaction. The term "free primary amino group" refers to an unsubstituted amine such a R-NH$_2$, where R refers to an organic residue bonded by a carbon-nitrogen bond to the amine.

In the peptide synthesis embodiment, the second substrate is an amino-protected amino acid or amino-protected peptide with at least one carboxylic acid ester. The term "amino-protected" refers to an amino acid or a peptide in which each amino group is covalently linked to a protecting group such as an acetyl, an amide, a tert-butyloxycarbonyl, or a trifluoroacetyl group, which prevents the amino group from participating in the reaction. The first substrate and the second substrate are dissolved together in a polar solvent, mixed with a solid support such as silica gel, and both substrates adsorb to the solid support. The polar solvent is then removed under vacuum. The combined first and second substrates and solid support are then mixed with a non-polar solvent such as n-hexane and a peptidase such as alpha-chymotrypsin. The enzyme catalyzes the aminolysis of the carboxylic acid ester to make a peptide bond to form the desired peptide product.

A further embodiment of the invention provides methods for the synthesis of a glycerol phosphate. Suitably, a hydrophilic substrate such as glycerol is adsorbed to a solid support such as silica gel and mixed with a non-polar solvent such as t-butylmethylether. To this mixture is added a phosphate donor such as a phosphate ester of an alcohol or of a phenol, or a carboxylic acid-phosphoric acid mixed anhydride. The reaction is catalyzed by a phosphatase such as acid phosphatase from potato. The phosphatase catalyzes the transfer of the phosphoryl moiety to the primary alcohol functions of glycerol to form the glycerol phosphate. This method may also be applied to the enzymatically catalyzed synthesis of phosphates of other alcohols, of sugars, and of nucleosides. Examples of phosphate group donors which may be employed are n-butylphosphate, methoxycarbonylphosphate, and vinylphosphate. Examples of other hydrophilic substrates which may be employed are dihydroxyacetone, glucose, and thymidine. The enzyme catalyst may be an alkaline phosphatase, for instance, from *E. coli*. Such reactions may produce, for instance, dihydroxyacetone-1-phosphate, D-glucose-6-phosphate, or thymidine-5'-phosphate, respectively.

A further embodiment of the invention provides compositions of hydrophilic substrates adsorbed to a solid support. When the adsorbed substrate is an alcohol or a carbohydrate, the ratio of substrate to solid support is preferably in the range of about 1.0:0.3 to about 1.0:10.0, more preferably 1.0:5.0, most preferably 1.0:1.0 (g:g). The composition may also comprise two substrates adsorbed to the solid support, as in a composition used for peptide synthesis. In this case, the ratio of the combined substrates to solid support is preferably in the range of about 1.0:0.6 to about 1.0:10.0, more preferably 1.0:5.0, most preferably 1.0:1.0 (g:g).

In the compositions, the hydrophilic substrate is dispersed in a thin layer of molecules on the surface of a finely divided solid support such as silica gel to provide a large exposed surface area of substrate. In compositions having two substrates adsorbed to the solid support, the substrates are also dispersed in thin molecular layers on the surface of the support. It is postulated that this dispersion allows the adsorbed substrate(s) to undergo rapid two-dimensional diffusion from the hydrophilic support through lipophilic interfaces to reach the enzyme active site. Preferably, the surface of the solid support is fully saturated with the hydrophilic substrate(s) in order to present the maximum number of reactive molecules to the enzyme, thus speeding the reaction. On the macromolecular level, the new compositions, comprising one or two hydrophilic substrates adsorbed to the solid support, take the form of a free-flowing powder.

The actual ratio of substrate(s) to solid support in a given composition can be determined using methods well known in the art of organic chemistry. For instance, the composition can be heated at 800° C. for several hours, and the loss of weight determined in comparison to a control (solid support without substrate).

The following examples illustrate specific embodiments of the present invention.

EXAMPLE 1

This example demonstrates the efficacy of various types of solid support. One gram of glycerol was mechanically mixed with 1 gm of silicagel (230–400 mesh, Merck), or other solid support (see Table 2) until a homogeneous, free flowing powder was obtained. The glycerol adsorbed to solid support was then mixed with 0.4 gm of vinyllaurate as acyldonor, and 100 mg of immobilized preparation of lipase from *Mucor mihei* (Lipozyme, Novo), in 10 ml of t-butylmethylether (t-BuOMe). As a control, the same amounts and types of substrates, biocatalyst, and solvent were mixed without added solid support. The mixtures were stirred for the indicated number of days (see Table 2) at 25° C. at atmospheric pressure. The enzyme was removed by filtration and the products were recovered from the organic phase by evaporation of the organic solvent. The products were analyzed qualitatively by thin-layer chromatography (TLC), followed by quantitative analysis using gas chromatography (GC).

The control mixtures (i.e. without solid support to adsorb glycerol) remained biphasic and the enzymes precipitated at the interphase leading to a gel which proved impossible to recover. Thus, no conversion was observed in the control mixtures without added support after 7 days.

Results were expressed as the percent of vinyllaurate converted to mono- di- and triglycerides (Table 2). The product composition was a consequence of the regioselectivity of the biocatalyst, which in this case, the lipase from *Mucor mihei*, was relatively selective for the one and three hydroxyl groups of glycerol, resulting in a preponderance of mono- and diglyceride products.

As shown in Table 2, the most efficient supports were silicagel (Aerosil), Florisil, and activated charcoal. However, all the supports listed are potentially useful.

TABLE 2

Enzymic esterifications of glycerol on different supports

| Carrier | t(d) | % conv. | Mono- | Di- | Tri- |
|---|---|---|---|---|---|
| Inorganic | | | glycerides | | |
| SiO$_2$ | 3 | 100 | 30 | 70 | — |
| Florisil | 2 | 95 | 30 | 65 | — |
| | 7 | 100 | 30 | 65 | 5 |
| | 14 | 100 | 30 | 60 | 10 |
| Chromosorb WAW | 2 | 60 | 10 | 50 | — |
| | 7 | 70 | 20 | 50 | — |
| | 14 | 95 | 35 | 60 | — |
| Chromosorb WHP | 2 | 70 | 30 | 40 | — |
| | 3 | 80 | 20 | 60 | — |
| | 7 | 85 | 25 | 60 | — |
| | 14 | 95 | 35 | 60 | — |
| Volaspher | 2 | 60 | 30 | 30 | — |
| | 3 | 80 | 20 | 60 | — |
| | 7 | 90 | 30 | 60 | — |
| | 14 | 951 | 35 | 60 | — |
| Celite 545 | 2 | 60 | 20 | 40 | — |
| | 3 | 85 | 25 | 60 | — |
| | 7 | 95 | 30 | 65 | — |
| | 14 | 95 | 30 | 65 | — |
| Celite 535 | 2 | 60 | 20 | 40 | — |
| | 3 | 85 | 25 | 60 | — |
| | 7 | 95 | 30 | 65 | — |
| | 14 | 100 | 30 | 70 | — |
| activated charcoal | 2 | 60 | 40 | 20 | — |
| | 3 | 95 | 25 | 70 | — |
| | 7 | 100 | 30 | 70 | — |
| | 14 | 100 | 30 | 70 | — |
| porous glass beads 345 Å pore size | 2 | 95 | 30 | 65 | — |
| | 7 | 100 | 30 | 65 | 5 |
| | 14 | 100 | 30 | 60 | 10 |
| porous glass beads 810 Å pore size | 2 | 95 | 30 | 65 | — |
| | 7 | 100 | 30 | 65 | 5 |
| | 14 | 100 | 30 | 60 | 10 |
| aluminum oxide neutral | 2 | 60 | 20 | 40 | — |
| | 3 | 85 | 25 | 60 | — |
| | 7 | 95 | 30 | 65 | — |
| | 14 | 100 | 30 | 70 | — |
| aluminum oxide basic | 2 | 60 | 20 | 40 | — |
| | 3 | 85 | 25 | 60 | — |
| | 7 | 95 | 30 | 65 | — |
| | 14 | 100 | 30 | 70 | — |
| organic supports | | | | | |
| Triacetylcellulose | 2 | 50 | 10 | 40 | — |
| | 7 | 70 | 30 | 40 | — |
| | 14 | 80 | 30 | 50 | — |
| Triacetylcellulose crosslinked | 2 | 60 | 10 | 50 | — |
| | 7 | 70 | 30 | 40 | — |
| | 14 | 80 | 30 | 50 | — |
| Starch | 2 | 3.5 | 5 | 30 | — |
| | 7 | 50 | 15 | 35 | — |
| | 14 | 75 | 25 | 50 | — |

EXAMPLE 2

In order to determine the effects of different solvents on the rates of conversion of glycerol to products, the experimental protocol of Example 1 was repeated, using silicagel as solid support, and using the solvents listed in Table 3.

The reactions were carried out at 25° C. for 24 hours, after which the percent molar conversion of vinyllaurate to products was measured as in Example 1. The activity was calculated as % molar conversion divided by time. Results are listed in Table 3 as relative activity, based on the reaction rate with n-hexane as 100%.

As shown in Table 3, a wide variety of solvents were suitable for the reaction. Due to their high relative activity, n-hexane, toluene or t-BuOMe may be the solvents of choice for many types of reactions. The other listed solvents may be useful in cases where the acyldonor is insoluble (or little soluble) in hexane, toluene, or t-BuOMe.

TABLE 3

Esterifications in organic solvents

| Solvent | rel. activity |
|---|---|
| n-hexane | 100 |
| toluene | 96 |
| t-BuOMe | 82 |
| Et$_2$O | 79 |
| methylisobutylketone | 68 |
| vinylacetate | 63 |
| ethylacetate | 53 |
| t-butanol | 45 |
| acetone | 43 |
| dichlormethane | 42 |
| THF | 42 |
| acetonitrile | 23 |
| DMF | — |
| DMA | — |
| DMSO | — |

EXAMPLE 3

These experiments were designed to determine which types of lipase preparations would be sufficient to catalyze an esterification reaction according to the method of the invention.

EXAMPLE 3A

Glycerol (0.92 g, 10 mmol) was mixed mechanically with 1.0 g Silicagel (Merck 230–4007 mesh) until the glycerol liquid was completely absorbed. The free flowing, dry powder was mixed with 10 g t-BuOMe and 5.42 g (24 mmol) vinyllaurate (molar excess) to which was added either 150 mg of crude lipase from *Pseudomonas fluorescens* (Amano Pharmaceutical Co., Nagoya, Japan) or 324 mg of Lipozyme.

The reaction catalyzed by Lipozyme was nearly complete after 3 hours. Products from the Lipozyme reaction were analyzed by TLC. After removal of the solid components by filtration and during evaporation of the solvent 4.9 g (100%) of crude 1.3-dilaurin crystallized out. Recrystallization from n-pentane produced 4.6 g (95%) of pure 1.3-dilaurin, white crystals mp 57° C. Percent yields were calculated based on molar conversion of glycerol to product.

The reaction mixture from *P. fluorescens* was filtered after 30 hours, the filter was washed twice with 20 ml tBuOMe and the solvent was removed in vacuo (rotovapor). The resulting crude product mixture (4.7 g, 96%) was separated by LC on SiO$_2$ producing 0.5 mmol (5%) Trilaurin, 8.54 mmol (85%) 1.3-Dilaurin and 1.1 mmol (11%) monolaurin. Percent yields were calculated based on molar conversion of glycerol to products.

EXAMPLE 3B

In order to determine the time dependence of esterification reactions on the specific enzymes employed, the following experiments were carried out using the same conditions as outlined in Example 1 (molar excess of glycerol) with the exception that the following enzyme preparations were used: *Rhizopus delemar, Candida cylindracea, Penicillium cyclopium* (Amano Pharmaceutical Co., Nagoya, Japan). The mixtures wre stirred at room temperature at 750 rpm and samples were drawn at the times indicated in FIG. 1 for analysis (TLC, $Et_2O$:n-hexane, 1:1, $I_2$-development, verified by GC).

The reaction catalyzed by lipase from *R. delemar* was, essentially complete by 45 hours, as only traces of the original starting amount of vinyllaurate remained. The lipase preparations from *P. cyclopium* and *C. cylindracea* were somewhat less efficient as the reactions were about 80% to 90% complete after 100 hours.

EXAMPLE 4

This experiment was designed to test whether the method of the invention could be scaled up for industrial use.

Glycerol (46 g, 0.5 mol) was mechanically adsorbed on 46 g silicagel and suspended in 1 liter of tBuOMe to which 226 g vinyllaurate had been added. After addition of 1.0 g Lypozyme, the mixture was stirred at room temperature for 48 hours. After removal of the solid components by filtration and evaporation of the solvent, 226 g of crude glycerides (85% 1,3-dilaurin) were obtained. The glycerides were dissolved in n-hexane and the solution was filtered over 300 g silicagel. The resulting solution was cooled to –30° C. resulting in 160 g (70%) of 1,3-dilaurin; the remaining products were recovered from the mother liquids. By recrystallization from n-hexane, 1,3-dilaurin was obtained in isomerically pure form (see Example 1 above).

EXAMPLE 5

This example demonstrates the preparation of glycerides from various vinylesters.

Glycerol (10 mmol) was adsorbed to 1 gm of silicagel, then suspended in 10 ml tBuOMe. Vinylester (vinylvalerate, caprylate, laurate, or palmitate) was added in the amount of 20 mmol, after which 50 mg of Lipozyme was added. The mixtures were stirred for 24 hours at room temperature. After removal of the enzyme-and silicagel, the solvent was evaporated to yield crude products. The crude products were dissolved in n-hexane, filtered over silicagel and cooled to –30° C. The resulting mixture contained 85–90% of 1,3-diglycerides with >95% purity.

EXAMPLE 6

This experiment was designed to test the effect of inclusion of molecular sieves to remove water from the reaction mixture during the direct esterification of glycerol with fatty acids.

Carboxylic acids [caprylic acid, C8; lauric acid, C12; palmitic acid, C16; 20 mmol each] and 10 mmol of glycerol preadsorbed to 1 gm of silicagel were suspended in 20 ml of tBuOMe. After addition of 50 mg immobilized lipase from Mucor mihei and 3 g 3 Å molecular sieves, the mixture was stirred for 48 hours at room temperature. After removal of all solids by filtration, the organic phase was washed with $NaHCO_3$-solution to remove traces of the fatty acids. After the separation steps described in Example 3, 1,3-diglycerides were obtained typically in yields from 65–85%.

EXAMPLE 7

This experiment was designed to demonstrate the esterification of ethylene glycol.

Ethyleneglycol (0.621 g, 10 mmol) was mixed mechanically with 1 g Silicagel (Merck 230–400 mesh) until the liquid was completely absorbed. The free flowing, dry powder was mixed with 12 g t-BuOMe and 4.75 g (21 mmol) vinyllaurate to which 150 mg of crude lipase from Pseudomonas sp. was added. The mixture was stirred at room temperature at 750 rpm for 8 hours after which the reaction was complete. TLC analysis showed no trace of starting material, i.e. quantitative conversion of substrates was achieved. Ethyleneglycoldilaurate in the amount of 4.0 gm (91%) was isolated.

EXAMPLE 8

This example demonstrates the production of polyesters.

Ethyleneglycol (0.621 g, 10 mmol) adsorbed on 1 g of $SiO2$ (silicagel) was reacted with 2.0 g (10.09 mmol) of divinyladipate in 10 g of t-BuOMe in the presence of 150 mg of crude lipase from *Pseudomonas fluorescens*. After 8 days the mixture was analyzed and found to contain a mixture of polyesters.

EXAMPLE 9

This experiment was designed to assess the dependence of the reaction rates on the method of preparing the adsorption of hydrophilic substrate. Percent adsorption was determined by collecting a sample of the silicagel/glycerol complex and (a) extracting the glycerol from the silicagel by washing with water, and quantifying the amount of glycerol by conventional chromotographic or enzymated methods, or alternatively by (b) drying at room temperature under vacuum and determining the weight increase.

Preparation 1.1.

As described in the above examples, glycerol was mechanically mixed with an equal amount of silicagel (230–400 mesh, Merck) until a homogeneous, free flowing powder was obtained.

Preparation 1.2.

The glycerol was dissolved in a minimum quantity (1g/10 ml) methanol (MeOH) to which an equal amount of silica gel was added. After stirring for two hours the silica gel was isolated by filtration and the filter cake dried in air. Only about 70% of the original starting amount of glycerol remained adsorbed on the silicagel in this preparation.

Preparation 1.3.

The glycerol was mixed with a minimum quantitiy of acetonitrile (1g/10ml) and adsorbed onto silicagel. The silicagel was isolated as in 1.2 above.

Only about 65% of the original starting amount of glycerol remained adsorbed on the silicagel.

Preparation 1.4.

The glycerol was mixed with MeOH and adsorbed onto silicagel as in Preparation 1.2 above. The MeOH was removed from the suspension on a rotavapor in vacuum.

Preparation 1.5.

This preparation was the same as Preparation 1.4, with the exception that acetonitrile was used in place of MeOH.

All glycerol preparations were then esterified using 50 mg of an immobilized preparation of lipase from *Mucor mihei* (Lipozyme, Novo) as biocatalyst and 2.0 g vinyllaurate as acyldonor, in 8.0 ml t-BuOMe with 0.5 gm glycerol adsorbed on silicagel. The reactions were monitored via the consumption of vinyllaurate (FIG. 2).

Figure 2:
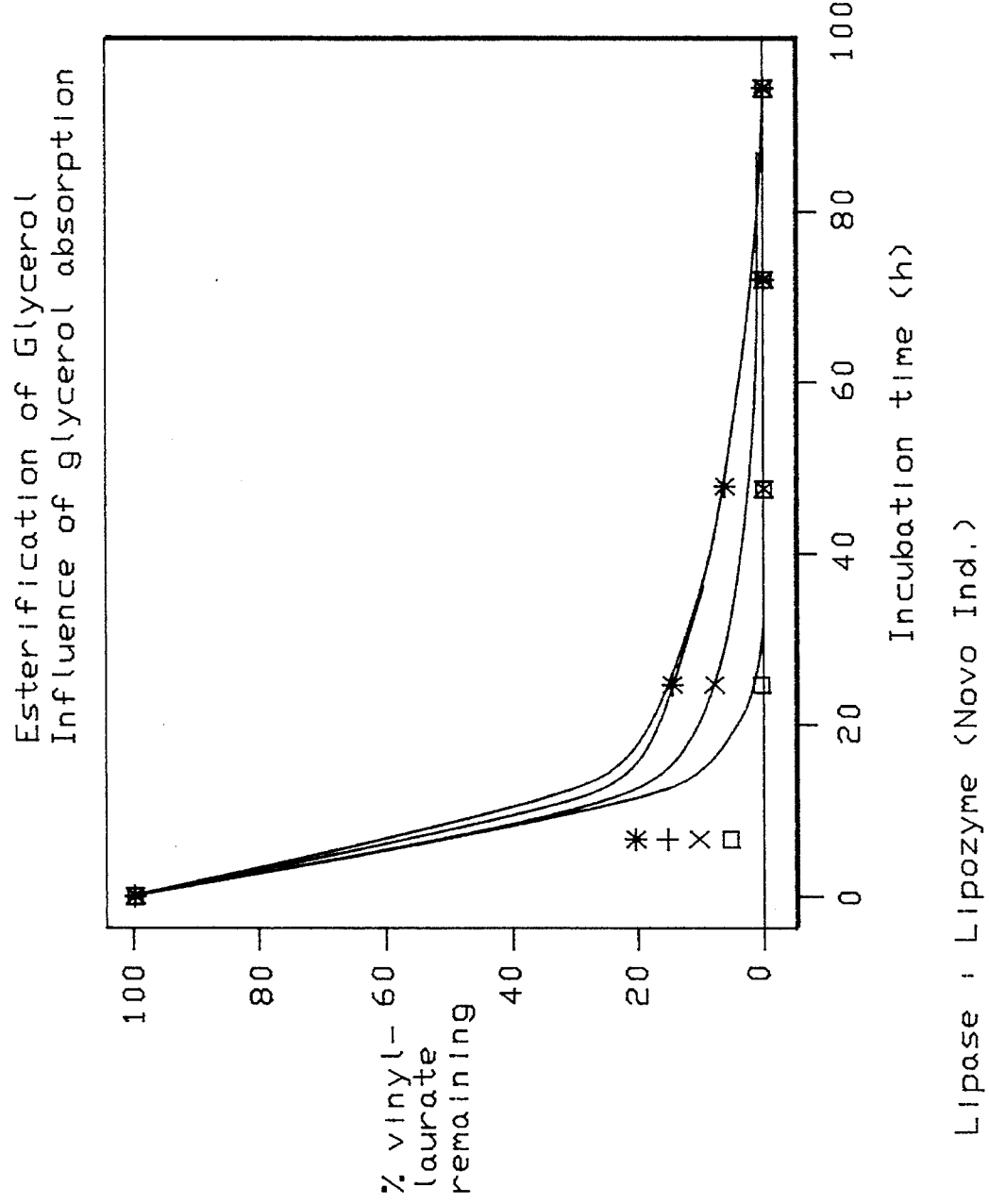
FIG. 2 depicts the effects of different methods of adsorbing glycerol to solid support on the rate of esterification.

As shown in FIG. 2, all the above preparations yielded satisfactory results. Preparation 1.4 (adsorption from MetOH) produced the most homogeneous silicagel/glycerol preparation with the best handling characteristics.

It should be noted that a hydrophobic solvent such as t-BuOMe was not essential for the esterification in this example since the acyldonor, vinyllaurate, was a liquid. The adsorbed glycerol, together with the biocatalyst, may be dispersed directly in the liquid second substrate. The rate of conversion, however, may be different.

EXAMPLE 10

This experiment was designed to assess whether it was necessary to pre-adsorb the hydrophilic substrate before conducting the reaction.
Preparation 2.1.
This was the control preparation in which the glycerol was pre-adsorbed on the silicagel as in Example 9, Preparation 1.1.
Preparation 2.2.
In a 10 ml flask 0.47 g (5 mmol) of glycerol, 2 g (10 mmol) of vinyllaurate and 8 ml of t-BuOMe were thoroughly mixed. To the formed emulsion, 0.5 g of silicagel were added and the mixture was stirred for about 1–2 minutes. Then 50 mg of Lipozyme was added and the resulting mixture was stirred for a total of 24 hours. At regular intervals, samples were drawn and analyzed.
Preparation 2.3.
As in Preparation 2.2, the glycerol, vinyllaurate, and t-BuOME were mixed to form an emulsion. In this case, the Lipozyme was added and stirred for 1–2 minutes prior to adding the silicagel.

Figure 3:
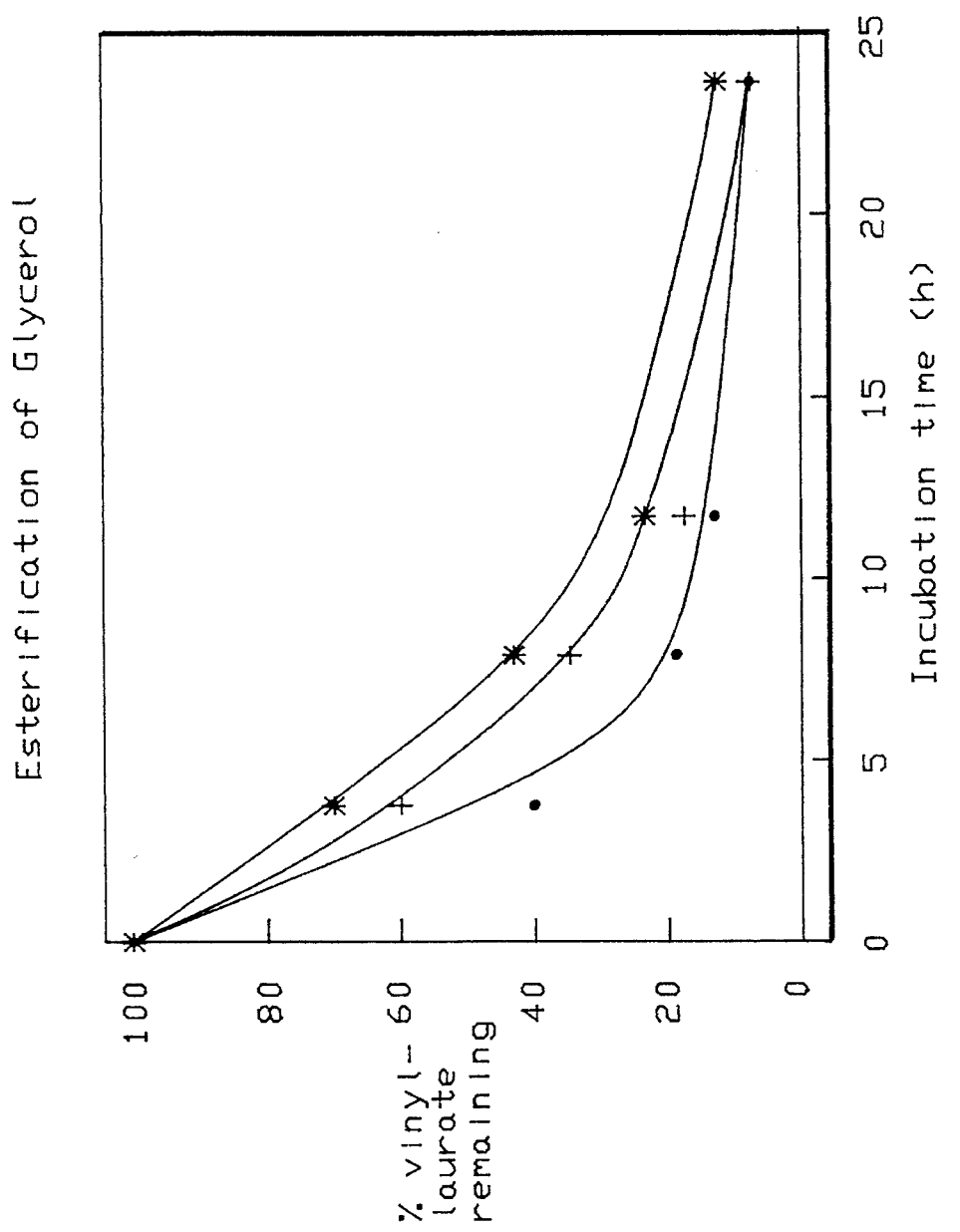
FIG. 3 depicts the effect of the order of mixing substrates, solid support, and enzyme on the rate of esterification of glycerol.

The results (FIG. 3) showed that rates of conversion were comparable among all three preparations. Preparation 2.1 was the fastest; however, when silicagel was added later (2.2 and 2.3) the reaction rate was satisfactory due to adsorption of glycerol in situ onto the silicagel.

EXAMPLE 11

This experiment was designed to determine whether solid, hydrophilic alcohol could be esterified using the method of the invention.
Preparation 3.1.
Sorbitol was mechanically mixed with an equal amount of silicagel using a mortar and pestle until a free flowing, homogeneous appearing mixture was obtained.
Preparation 3.2
Sorbitol was dissolved in a minimum quantity of 99% McOH to which an equal amount of silicagel was added. After stirring for 2 hours, the silicagel was recovered by filtration and dried. Only 45% of the original starting amount of sorbitol remained on the support.
Preparation 3.3.
Sorbitol was dissolved in a minimum quantity of 99% MeOH to which an equal amount of silicagel was added. The solvent was then removed under vacuum using a rotavapor. The residue, a free flowing powder, was used directly in the esterification reaction.

Figure 4:
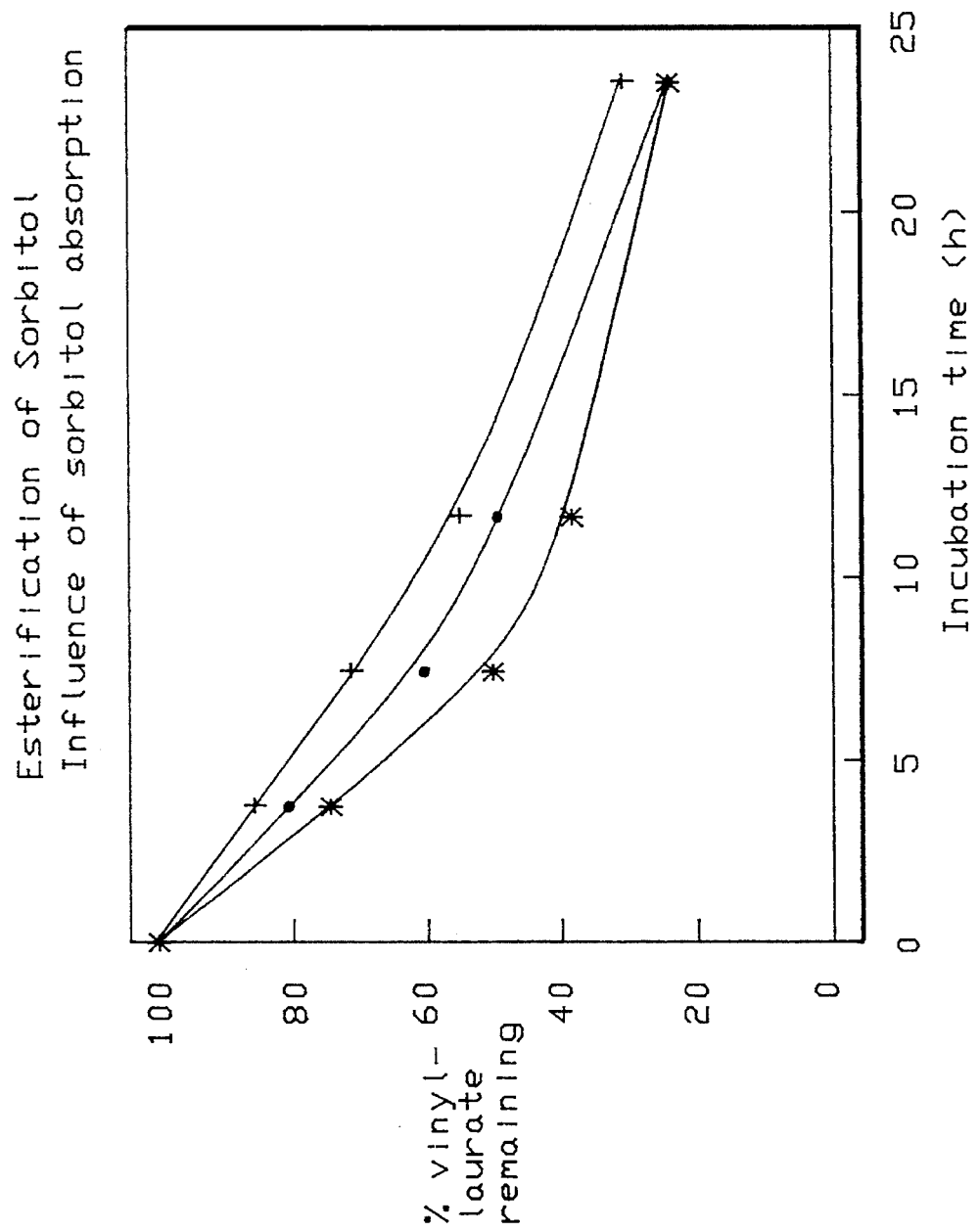
FIG. 4 depicts the effects of different methods of adsorbing sorbitol to solid support on the rate of esterification of sorbitol.

Sorbitol (0.8 g, corrected for the amount remaining after adsorption), 0.4 g vinyllaurate, 50 mg immobilized lipase from *Mucor mihei* (Lipozyme, Novo) and 8 ml t-BuOMe were mixed and stirred for a total of 24 hours. At regular intervals samples were drawn from the mixture and analyzed by TLC (FIG. 4). From all three adsorbed preparations, esterification was observed. Clearly the fastest reaction was observed with the material prepared according to method 3.3 (adsorption from MeOH and solvent removal under vacuum).

EXAMPLE 12

This experiment was designed to assess the effect on esterification of the ratio of solid support to glycerol.

Glycerol (0.92 g, 10 mmol) was adsorbed on varying amounts (0, 0.3, 0.6 and 1 g) of silicagel (Merck 230–400 mesh) and esterified as in Example 1 in t-BuOMe with 5.42 g (24 mmol) of vinyllaurate as acyldonor. As esterification catalyst, 150 mg of lipase derived from Pseudomonas fluorescens were employed.

After an incubation time of 30 hours all reaction mixtures were analyzed by TLC and worked up for quantitative product isolation. Only the samples containing 0.6 and 1 g of silicagel showed complete conversion of glycerol to ester product. The results are summarized in Table 4. For efficient conversion, it is preferable to use a silicagel:glycerol ratio greater than about 0.6:10 (g:mmol).

TABLE 4

| (g) $SiO_2$ | conversion | % yield | Mono- | Di-laurate | Tri- |
|---|---|---|---|---|---|
| 0 | incomplete | trace | — | — | — |
| 0.3 | incomplete | 45 | 42 | — | — |
| 0.6 | complete | quant. | — | 82 | 18 |
| 1.0 | complete | quant. | 11 | 8.5 | 4 |

EXAMPLE 13

This experiment was designed to assess whether a solid carbohydrate, glucose, could be esterified according to the method of the invention.

D-glucose (0.412 g, 2.29 mmol) adsorbed on 0.588 g of silicagel was added to a mixture of 20 ml t-BuOMe and 30 mmol of either vinylacetate, vinylbutyrate, or vinyllaurate as acyl donor. After addition of 200 mg lipase derived from Pseudomonas fluorescens the mixtures were stirred for 14 days. The reaction mixtures were then filtered and the filter cakes were washed thoroughly with fresh t-BuOMe. The solvent was removed on a rotavapor and the residue dried on a high vacuum line.

From the reactions using vinylacetate as acyl donor, 370 mg of a yellow syrup were obtained and separated by chromotography yielding three fractions:
(1) 75 mg syrup RF=0.96 (front); d-glucose-2,4,6-triacetate.
(2) 185 mg syrup RF=0.79; d-glucose-2,6-diacetate.
(3) 100 mg colorless crystals, RF=0.54; D-glucose-6-acetate.
(Solvent for chromatography: EtOAc: 2-propanol:$H_2O$=600:270:130; Nuclear Magnetic Resonance [NMR] analysis conducted at 400 MHz.)
From the reaction using vinylbutyrate as acyldonor, 580 mg of a colorless syrup was obtained. Separation by chromatography on silicagel yielded 60 mg crystalline material, RF=0.69; d-glucose-6-butyrate.

From the reaction using vinyllaurate as acyl donor, 5.8 g of a colorless liquid remained, consisting mainly of excess vinyllaurate and lauric acid. TLC analysis revealed that mainly product(s) of low polarity with RF=0.94 had been formed. After a few days of standing at room temperature, the mixture crystallized and the crystals were isolated by filtration. NMR analysis demonstrated the formation of D-glucose-6-laurate.

As a control, esterification of D-glucose without solid support was attempted. 1.8 g (10 mmol) of anhydrous D-glucose was added to a mixture of 4.6 ml (50 mmol) vinylacetate in 20 ml of t-BuOMe. After addition of 300 mg lipase derived from Pseudomonas fluorescens the mixture was stirred at room temperature for 14 days. After that the reaction mixture was filtered and the filter cake washed with fresh t-BuOMe. The solvent was removed on a rotavapor and the residue dried on a high vacuum line. Obtained were 60 mg of a colorless syrup, corresponding to a yield of less than 5% based on conversion of D-glucose.

In summary, the results from this experiment indicated that D-glucose could be esterified according to the method of the invention. The main products were D-glucose-6-acetate, D-glucose-2,6-diacetate, and D-glucose-2,4,6-triacetate. The yields ranged from 30% to 50%.

EXAMPLE 14

This example demonstrates the production of isomerically and chemically pure 1-monoglyceride by direct esterification of glycerol with free carboxylic acid. In this context, the term "chemically pure" refers to a preparation of 1-monoglyceride substantially free of 2-monoglycerides, diglycerides, and triglycerides. The term "isomerically pure" refers to a preparation of 1-monoglyceride substantially free of 2-monoglycerides.

The amounts and types of substrates and silicagel used are indicated in Table 5. The glycerol was preadsorbed onto the silicagel as in Example 3, then mixed in the reactor vessel (FIG. 7,7) with the indicated carboxylic acid and 100 mg of Lipozyme suspended in 80 ml of a 1:1 mixture of t-BuOMe/n-hexane. The reactor 7 was connected with the separator 11 via a column filled with 3 Å molecular sieves 6 to remove water produced in this reaction. The reaction mixture was stirred in the reactor 7 at a temperature of 25° C. at atmospheric pressure.

The separator (FIG. 7,11) was cooled to 2° C. The solution was circulated continuously from the reactor 7 (maintained at 25° C.) to the separator 11 (maintained at 2° C.), and back to the reactor 7 at a rate of 1 ml/min. Two filter discs, one in the outlet from the reactor 8 and one in the outlet from the separator 12, were employed to retain solid materials. A precipitate was observed forming in the cooled separator 11. At the times indicated in Table 5, the reaction was terminated and the product precipitated in the separator 11 was collected by simple suction filtration. The precipitate was washed with two volumes of cold n-hexane and analyzed by gas chromotography of the trimethylsilylether (TMS) derivative. The TMS derivative was produced by reacting a hydroxylgroup with trimethylsilylchloride to produce the volatile TMS derivative for analysis by gas chromatography. The pure 1-monoglyceride products were obtained with isomeric and chemical purities greater than 95%. As shown in Table 5, column 1, when glycerol was used in excess, 90% yield was obtained within 48 hours (percent yield based on molar conversion of lauric acid). When stoichiometric amounts of reactants were used (columns 2 and 3), the reactions progressed more slowly; a yield of 86% was obtained by 120 hours (Table 5).

TABLE 5

| | | | |
|---|---|---|---|
| Glycerol | 4.0 g | 1.85 g | 1.85 g |
| Silicagel | 4.0 g | 1.9 g | 1.9 g |
| Carboxylic acid | 3.0$^l$ g | 4.0$^l$ g | 6.0$^s$ g |
| Solvent | 80 ml | 80 ml | 100 ml |
| % Yield: | | | |
| 24 hrs. | | 24% | |
| 48 hrs. | 90% | | 29% |
| 120 hrs. | | 86% | | l = lauric acid
s = stearic acid

EXAMPLE 15

This experiment demonstrates the production of chemically pure 1-monolaurin by esterification of glycerol with vinyllaurate.

The amounts of substrates and silicagel are indicated in Table 6. As in Example 3, the glycerol was preadsorbed to the silicagel, then mixed in the reactor (FIG. 6,1) with the vinyllaurate and 100 mg of Lipozyme in 80 ml of a 1:1 mixture of t-BuOMe/n-hexane.

The reactor 1 was connected with the separator 5 as shown in FIG. 6. This system differs from that used in Example 14 only in the elimination of the molecular sieves in the connector. Molecular sieves are not necessary in this reaction, since water or alcohol is not a by-product.

The solution was stirred in the reactor 1 at a temperature of 25° C. at atmospheric pressure. As in Example 14, the separator 5 was cooled to 2° C. and the solution was circulated through the system at a rate of 1 ml/min for the indicated time. The precipitate was collected, washed, and analyzed as in Example 14. As shown in Table 6, the pure 1-monolaurin product was obtained in yields of 27% to 90% with isomeric purity greater than 97% as determined by gas chromatography analysis of the TMS derivatives.

TABLE 6

| | | |
|---|---|---|
| Glycerol | 4.0 g | 1.85 g |
| Silicagel | 4.0 g | 1.9 g |
| Vinyl-laurate- | 2.0 g | 4.5 g |
| Solvent | 80 ml | 80 ml |
| % Yield | | |
| 24 hrs. | | 27% |
| 48 hrs. | 73% | |
| 196 hrs. | | 90% |

EXAMPLE 16

This experiment was designed to test the method of the invention in the larger scale production of 1-monolaurin through the enzymatic esterification of glycerol with methyllaurate.

Glycerol (23 g, 250 mmol) was adsorbed on 25 g of silicagel as in Example 1. Methyllaurate (53 g, 0.25 mol) and 500 mg Lipozyme were suspended with the adsorbed glycerol in 500 ml of a 1:1 mixture of t-BuOMe/n-hexane in the reactor depicted in FIG. 6. Molecular sieves of pore size 4 Å were employed to remove the methanol by-product, thereby promoting the reaction in the desired direction of reverse hydrolysis.

As in Example 14, the separator was cooled to 2° C. and the solution was circulated through the system. The precipitate was collected from the separator and analyzed as in Example 14. After 48 hours, 17.8 g (26% yield) 1-monolaurin was collected from the separator. After 144 hours, 45.9 g (67% yield) of this material was produced with >99% isomeric and chemical purity.

EXAMPLE 17

This example demonstrates the production of pure 1-monolaurin by esterification of glycerol with the triglyceride trilaurin as acyldonor. The experiment was conducted as in Example 15, with the exception that instead of Lipozyme, 100 mg of immobilized lipase from *P. fluorescens* was used (Amano Pharmaceutical Co, Ltd., Nagoya, Japan). Lipase from *P. fluorescens* has activity towards all three positions of the triglyceride and thus effectively removes all the acyl groups from the acyldonor. In contrast, the lipase from *M. mihei* (Lipozyme) exhibits specificity towards the 1 and 3 positions of the triglyceride and would not be able to effectively remove the acyl group from the 2 position of trilaurin. The amounts of substrates and solid support are indicated in Table 7. As shown in Table 7, yields of between 21% and 80% were obtained with an isomeric purity of 1-monolaurin greater than 95%. When glycerol was used in molar excess (column 1, Table 7), the reaction proceeded rapidly to 80% yield within 48 hours. When stoichiometric amounts of reactants were employed (column 2, Table 7), the reaction proceeded more slowly to 75% yield after 96 hours.

TABLE 7

| Glycerol | 4.0 g | 3.7 g |
| --- | --- | --- |
| Silicagel | 4.0 g | 4.0 g |
| Trilaurin | 4.0 g | 13.04 g |
| Solvent | 80 ml | 80 ml |
| % Yield: | | |
| 24 hrs. | | 21% |
| 48 hrs. | 80% | |
| 96 hrs. | | 75% |

EXAMPLE 18

This example demonstrates the production of pure 1-monopalmitin by the esterification of glycerol with methylpalmitate. The experiment was conducted as in Example 15 using 5.4 g (20 mmol) of methylpalmitate, 1.85 g (20 mmol) of glycerol adsorbed on 1.9 g of silicagel and 100 mg of Lipozyme in 100 ml of the solvent mixture used in Example 15.

After 48 hours, 2.31 g (35% yield) of 1-monopalmitin with >97% isomeric purity was obtained.

EXAMPLE 19

This example demonstrates the use of solid support in a column as an alternative to the methods of preparation of adsorbed substrate employed in Example 9.

Glycerol (3.7 g, 20 mmol) was mechanically mixed with 4 g of silicagel and 100 mg of Lipozyme. The mixture was packed into a glass column (8 mm×15 cm). A solution of 9.0 g vinyllaurate in 20 ml of t-BuOMe was circulated via a membrane pump through the column at a rate of 5 ml/min for a total of 24 hours. The column was then flushed with 20 ml fresh t-BuOMe and all organic phases were removed. The remaining viscous material was dissolved in n-hexane and flash chromatographed through a short silica gel column. The solution was cooled to −20° C., which caused crude 1,3 dilaurate (about 95% pure) to crystallize out. After recrystallization from n-hexane, 8.2 g (90% yield) 1,3-dilaurin was obtained as white crystals with a chemical purity of greater than 99%, as determined by gas chromatography.

EXAMPLE 20

This example demonstrates the production of a peptide-ester. The hydrophilic substrate employed was Z-L-serine (Sigma Chemical Co., St. Louis, Mo.). The "Z" moiety is the carbobenzyloxy protection group which is covalently linked to the alpha-amino group of serine in order to prevent the formation of zwitterions and in order to provide only one nucleophilic group for acceptance of the acyl group.

Z-L-serine (0.4785 g, 2 mmol) was adsorbed on 2 g silicagel using acetone as solvent as described in Example 9, preparation 1.4. The resulting free-flowing powder was mixed with 20 mol t-BuOMe and 10 mmol of vinylvalerate (1.28 g) or 10 mmol of vinyllaurate (2.26 g). To this mixture was added 1 g of Lipozyme. The mixture was shaken at 350 rpm at 30° C. for 24 hours, after which all solids were removed by filtration. From the resulting organic phase, the solvent was removed by evaporation (rotavapor) and the resulting residue was flash chromatographed on silicagel to remove excess vinylvalerate or vinyllaurate (n-hexane:t-BuOMe, 1:1, followed by acetone:methanol, 4:1). After removal of all solvent the solid residue was recrystallized from n-hexane. Obtained from the reaction with vinylvalerate: 0.576 g (94 % yield) of Z-L-serine valerate as colorless crystals, m.p. 188°–189° C.;

$[\alpha]_D^{20}=-5.0°$ (c=1, CHCl$_3$).

Obtained from the reaction with vinyllaurate: 0.776 g (92% yield) of Z-L-serine laurate as colorless powder, m.p. 160°–162° C.;

$[\alpha]_D^{20}=+2.0°$ (c=1, CHCl$_3$).

EXAMPLE 21

This example demonstrates the production of a glycoside, 1-O-β-D-galatopyranosyl-n-dodecanol.

The hydrophilic substrate, o-nitrophenylgalactopyranoside (10.2 g, 32 mmol) is dissolved under ultrasonication in 150 ml of methanol warmed to 50°–60° C. The dissolved substrate is adsorbed onto 30 g of silica gel as described in Example 9, preparation 1.4. After removal of the solvent, the material is dried under vacuum to produce a free-flowing powder. The material is then mixed with 320 ml of n-hexane and 17.6 g (96 mmol) of n-dodecanol. The enzyme β-galactosidase (2750 U, Sigma Chemical Co., St. Louis, Mo.) is added and the mixture is stirred at room temperature for 24 hours. The solid materials are removed by filtration. From the organic phase, 11.0 g (60 mmol) of n-dodecanol and 4.4 g (31 mmol) of o-nitrophenol are recovered. The solid material is thoroughly extracted with 3×200 ml of methanol and all solid materials are removed by filtration. After removal of the solvent, 9.46 g (26 mmol) of 1-O-β-D-galactopyranosyl-n-dodecanol is obtained as semi-solid oily material.

EXAMPLE 22

This example demonstrates the synthesis of N-acetyl-L-tyrosine-L-phenylalaninamide.

N-Acetyl-L-tyrosine ethylester monohydrate [1 mmol; 269 mg] and L-phenylalaninamide hydrochloride [1 mmol; 201 mg] are dissolved in 20 ml MeOH. To this solution is added 5 g of silica gel, and the MeOH is removed under vacuum. The thus obtained material is mixed with 20 ml n-hexane, $Na_2CO_3.10\ H_2O$ [2 mmol; 572 mg], and 20 mg alpha-chymotrypsin. The mixture is stirred for 24 hours at room temperature, and the solvent is then removed by vacuum. The residue is then extracted with hot acetonitrile. HPLC analysis of the resulting solution indicates a conversion of greater than 90% at this point. The solution is concentrated by removing the remaining solvent under vacuum and the residue is recrystallized from acetonitrile. The resulting product is N-acetyl-L-tyrosine-L-phenylalaninamide in the amount of 259 mg (70%).

EXAMPLE 23

This example demonstrates the enzymatically catalyzed synthesis of N-acetyl-L-tyrosine-L-leucinamide.

N-Acetyl-L-tyrosine-ethyl ester monohydrate (1 mmol; 269 mg) and L-leucinamide hydrochloride (1 mol; 167 mg) are suspended in 20 ml t-BuOMe. To this suspension, $Na_2CO_3.10\ H_2O$ (2 mmol; 572 mg), silicagel (5 g), and alpha-chymotrypsin (20 mg) are added. The resulting mixture is stirred for 24 hours at room temperature. After removal of the solvent, the residue is extracted with hot acetonitrile. HPLC analysis indicates a conversion of greater than 95%. The isolated dipeptide (80%) is identified by comparison with a known sample.

EXAMPLE 24

This example demonstrates the enzymatically catalyzed synthesis of glycerol-1-phosphate.

Glycerol (10 mmol; 0.92 g) is adsorbed to an approximately equal amount of silica gel (1.0 g) and then suspended in 20 ml of t-BuOMe. To this mixture is added p-nitrophenylphosphate (10 mmol) followed by acid phosphatase from potato (1000 U; 200 mg). The mixture is stirred at room temperature for 24 hours. The solvent is removed by vacuum, the residue is thoroughly extracted with water (3×150 ml), and all solids are removed by filtration. The resulting aqueous solution is concentrated under vacuum to 75 ml and treated with a solution 21 mmol of $BaCl_2.2H_2O$ to form a precipitate. To the suspension is added 500 ml of 95% ethanol and the precipitate is allowed to settle overnight. The suspension is filtered and the solid material is dried over $CaSO_4$. Glycerol-1-phosphate (8.5 mmol) is obtained containing 94% of the title compound as the barium salt.

What is claimed is:

1. A method for producing an amphiphilic compound consisting essentially of:
    (a) mixing together the following substances in any order:
        a hydrophilic first substrate containing at least one hydroxyl group and a carbon bound to the oxygen of said at least one hydroxyl group, said first substrate being selected from the group consisting of glycerol, ethylene glycol, sorbitol and glucose,
        a solid support which results in the adsorption of at least 50% of said first substrate on the support, the ratio of said solid support to said first substrate being about 0.6:1.0 to about 10.0:1.0 (g:g),
        a solvent which is selected from the group consisting of n-hexane, toluene, t-butylmethylether, ethylene oxide, methylisobutylketone, vinylacetate, ethylacetate, t-butanol, acetone, dichloromethane, and tetrahydrofuran,
        a second substrate which is immiscible with said first substrate and which has at least one donatable leaving group, said second substrate being selected from the group consisting of carboxylic acids, esters, anhydrides and triglycerides, and
        a hydrolase which catalyzes a reaction between said two substrates to produce an amphiphilic compound, and
    (b) recovering said amphiphilic compound, said compound comprising said carbon from said first substrate and said donatable leaving group from said second substrate.

2. The method of claim 1 wherein said hydrolase is a carboxylic ester hydrolase.

3. The method of claim 1 wherein said second substrate is selected from the group consisting of vinyllaurate, vinyladipate, and vinylacetate.

4. The method of claim 1 wherein said second substrate is selected from the group consisting of caprylic acid, lauric acid, and palmitic acid.

5. The method of claim 1 further comprising the step of mechanically mixing said first substrate with said solid support before adding said second substrate and said hydrolase.

6. The method of claim 1 wherein said solid support is selected from the group consisting of silica gels, diatomaceous earths, clays, activated charcoals, carboxymethycellulose, cellulose esters, ion exchange resins, and insoluble polysaccharides.

7. A method for producing an amphiphilic compound consisting essentially of:
    (a) mixing together the following substances in any order to form a mixture:
        a hydrophilic first substrate having at least one hydroxyl group and a carbon bound to the oxygen of said at least one hydroxyl group, said first substrate being selected from the group consisting of glycerol, ethylene glycol, sorbitol and glucose;
        a solid support which results in the adsorption of at least 50% of said first substrate on the support, the ratio of said solid support being about 0.6:1.0 to about 10.0:1.0 (g:g), and a hydrolase;
    (b) packing said mixture into a column,
    (c) circulating a solvent and a second substrate through said column, wherein said solvent is selected from the group consisting of n-hexane, toluene, t-butylmethylether, ethylene oxide, methylisobutylketone, vinylacetates ethylacetate, t-butanol, acetone, dichloromethane, and tetrahydrofuran, and said second substrate has at least one donatable leaving group, is immiscible with said first substrate and is selected from the group consisting of carboxylic acids, esters, anhydrides and triglycerides, and said hydrolase catalyzes a reaction between said two substrates to produce an amphiphilic compound; and
    (d) recovering said amphiphilic compound, said compound comprising said carbon from said first substrate and said leaving group from said second substrate.

* * * * *